United States Patent [19]

Lampkin et al.

[11] Patent Number: 5,147,798
[45] Date of Patent: Sep. 15, 1992

[54] MONOPHENOTYPIC XENOGRAFT OF MEGAKARYOCYTIC LINEAGE AND ORIGIN

[75] Inventors: Beatrice C. Lampkin; David P. Witte; Richard E. Harris; Michael A. Liebermann, all of Cincinnati, Ohio

[73] Assignee: Children's Hospital Medical Center, Cincinnati, Ohio

[21] Appl. No.: 727,373

[22] Filed: Jul. 5, 1991

Related U.S. Application Data

[63] Continuation of Ser. No. 565,190, Aug. 8, 1990, abandoned, which is a continuation of Ser. No. 884,714, Jul. 11, 1986, abandoned.

[51] Int. Cl.$^5$ .................. C12N 5/00; C12N 5/08; C12P 21/02; C07K 15/06
[52] U.S. Cl. .................. 435/240.1; 435/240.2; 435/70.3; 435/70.4; 530/399; 530/827
[58] Field of Search ............ 435/240.1, 240.2, 240.21, 435/240.23, 240.25, 94, 68; 530/399, 828, 837, 838, 840

[56] References Cited

PUBLICATIONS

Tabilio et al., "Expression of Platelet Membrane Glycoproteins and β-Granule Proteins by a Human Erythroleukemia Cell Line (HEL)", EMBO, v. 3(2), 453–459, 1984.

Morgan et al., "Novel Peripheral Blood-Derived Human Cell Lines with Properties of Megakaryocytes", J. Cell Biology v 100, 565–573, Feb. 85.

Pantazis et al., "Platelet-Derived Growth Factor Polypeptides in Human Megakryoblastic-Like Cell Lines" Cancer Cells 3, 153–157, 1985 ed:Feramiso et al..

Fieshey, "Introduction" in *Culture of Animal Cells*, pp. 1–6, 1983.

*Primary Examiner*—John J. Doll
*Assistant Examiner*—George C. Elliott
*Attorney, Agent, or Firm*—Wood, Herron & Evans

[57] ABSTRACT

A continuous cell line of megakaryocytic origin is disclosed. This novel continuous cell line has been established in athymic nude mice. The cells of the established cell line monophenotypic for megakaryocytes is characterized as having multilobed nuclei and granular cytoplasm and being reactive for Factor VIII antigen, glycoprotein IIB-IIIa complex antigen and platelet peroxidase. The established cell line of this invention generates in isolatable quantities platelet-like factor IV, FGF-like, β-thromboglobulin-like and TGF-β-like growth factors. Methods for cultivating the established cell line, in a nude animal and isolating and purifying the proteins are also disclosed.

1 Claim, 10 Drawing Sheets

97
67
43
31
21

| LANE | SAMPLE | PROBE |
|---|---|---|
| 1 | 10ng PURIFIED TGF-B | anti-TGF-B |
| 2 | ACID EtOH EXTRACT OF TUMOR CELLS | anti-TGF-B |
| 3 | ACID EtOH EXTRACT OF TUMOR CELLS | anti-EGF |

MONOPHENOTYPIC XENOGRAFT OF MEGAKARYOCYTIC LINEAGE AND ORIGIN

This application is a file wrapper continuation of application Ser. No. 07/565,190, filed Aug. 8, 1990 which is a continuation of application Ser. No. 06/884,714, filed Jul. 11, 1986, both abandoned.

FIELD OF THE INVENTION

The present invention relates to a novel continuous xenograft and more particularly a novel continuous human cell line of megakaryocytic origin, a method of cultivating the xenograft, products generated by the xenograft and a method of producing those products.

BACKGROUND OF THE DISCLOSURE

Cell regulation is mediated by a wide variety of polypeptides. Historically, few of these polypeptides are produced in sufficient amounts to be isolated and characterized. Even in those situations where particular polypeptides are capable of isolation and characterization, the number of amino acids constituting the polypeptides normally preclude synthesis by conventional polypeptide bond formation in commercially useful amounts In the last few years, however, a number of discoveries relating to biotechnology have occured which at the present time promise opportunities for the detection, isolation and production in commercially useful amounts of naturally occurring proteins, which fulfill a wide variety of cell regulatory functions.

The ability to isolate, characterize and insert a gene into a replicating vector, such as a plasmid or phage, and transform a microorganism with the resulting hybrid has introduced new techniques, i.e., genetic engineering techniques, for the production of macromolecular polypeptides. These techniques not only afford the opportunity to obtain polypeptides in abundance, but allow for study of the polypeptides and use of the polypeptides in regulating cell functions in vitro and in vivo.

Because of the cumbersome nature and difficulties associated with synthesis and existence of introns present in chromosomal DNA, the messenger RNA is frequently the desired route where genetic engineering is involved. In each cell, there is continuously produced a large number of different messenger RNA molecules. Therefore, means must be provided for isolating the messenger RNA of interest from other messenger RNA molecules. Where a messenger RNA of interest is normally produced in only small amounts as compared to the total amount of messenger RNAs, it is frequently desirable, if not necessary, to obtain cells which enhance the amount of messenger RNA of interest present in the cell.

As an alternative to genetic engineering, the ability to culture cells offers an opportunity for the production of a wide variety of polypeptides. By isolating specific cells and establishing a culture, which can be expanded and maintained for extensive periods of time, one can directly produce the polypeptides of interest from the cultured cells. In this manner, one avoids the need to isolate the gene or messenger RNA of interest and perform the numerous complicated steps involved with successful genetic engineering.

The regulation of cell growth is a poorly understood topic. A large number of growth regulatory factors have been described heretofore which can either stimulate or inhibit cell growth. A total understanding of the integration of all the signals a cell receives from these factors has not yet been achieved. While such factors have been isolated from many sources, platelets are known to contain large quantities of a variety of potent growth factors. Platelet-derived growth factor (PDGF) and the transforming growth factors alpha and beta (TGF-$\alpha$, TGF-$\beta$) fall into this category. Not much is known concerning the physiological function of these factors, although roles have been postulated for both PDGF and TGF-$\beta$ in the process of arterial wall wound repair. PDGF is a very potent mitogen for smooth muscle cells, fibroblasts and glial cells. The addition of PDGF to such cells renders the cells competent to enter the cell cycle. A second set of growth factors, termed progression factors, are then believed to be required to progress the cells around the cycle. PDGF addition to cells also elicits a myriad of responses, although it is still not clear if all of these responses are required to elicit the mitogenic response. Structurally, PDGF consists of two non-identical subunits, designated the A and B chains, which are linked by disulfide bonds. Its molecular weight is between about 28-35,000 Daltons, depending on the degree of glycosylation of the sample. Separation of the subunits is believed to result in total loss of biological activity. Recently, it has been suggested that the B chain of PDGF is highly homologous to the predicted protein sequence of the oncogene (v-sis) of simian sarcoma virus (SSV). Indeed, SSV-infected cells either store or secrete a growth factor which is immunologically similar to PDGF. The biosynthesis of this protein has been studied in SSV transformed cells and has been shown to undergo extensive processing, although the major form appears to be a protein of 28,000 Daltons. A specific cell surface receptor for PDGF has been identified and is present on smooth muscle cells, fibroblasts, and glial cells. The apparent molecular weight of the receptor is 190,000 Daltons, and the receptor contains tyrosine kinase activity, as has been shown for both the EGF and insulin receptors. No studies have yet been reported on the biosynthesis or processing of platelet PDGF, nor has a role for the A chain been demonstrated. Indeed, it has recently been demonstrated that the B chain alone of PDGF is sufficient for mitogenesis, leaving the physiological significance of the A chain in doubt. Interestingly, both normal cells and transformed cells have been shown to secrete PDGF-like mitogens into the culture media. It seems likely that growth factors, including PDGF, have some role in normal cellular development, differentiation and tissue repair. The autonomy of transformed cells may be related to endogenous production of growth factors, including PDGF, which may lead to autocrine stimulation and constant stimulation of cell growth.

Fibroblast growth factor (FGF) was initially identified in 1975, Gospodarowicz, D.: *J. Biol. Chem.* 250:2515-2520(1975). *Leukemia Research* 8:769-81,1984; its exact chemical nature has remained obscure until only recently. At least two forms of FGF have been identified. One is of an acidic nature (pI=5.8), the other basic (pI=9.6). Both forms are present in bovine brain, and the basic form has also been found in bovine pituitary. It is also possible that basic FGF may be present in platelets as well. Both species of FGF will stimulate the growth of cells of mesodermal origin, although their potencies are different. The biological effects of FGF reported in the past are now being re-examined, as preparations used in the past were not pure. What is certain, however, is that FGF will stimulate both fibroblast and endothelial growth, as well as repress cell differentiation in cultured muscle cells. No data, however, is believed to be available concerning the biosynthesis of FGF.

The transforming growth factors (both alpha and beta) have very interesting properties. TGF-α was first found to be secreted by various transformed cells, and has since been shown to interact with epidermal growth factor (EGF) receptors, and to be structurally (although not antigenically) similar to EGF. TGF-α will elicit the same intracellular events as EGF, including cellular proliferation via binding to the EGF receptor. The molecular weights of various species of TFG-α's varies from about 6,000 to about 11,000 Daltons, and all consist of single polypeptide chains. Recently, a higher molecular weight form (about 25,000 Daltons) of TGF-α has been identified in platelets. This may represent a precursor form of other TGF-α's, although this has not yet been conclusively demonstrated. TGF-α, in conjunction with TGF-β, will allow fibroblasts to grow in soft agar, which is a typical property of transformed cells. Neither TGF-α or TGF-β by themselves can do this TGF-α has a molecular weight of 25,000 Daltons and consists of a homodimer. The subunits are held together by many disulfide linkages, and destruction of the linkages also leads to a loss of biological activity. TGF-β was also initially found to be secreted by transformed tissues. Platelets are a major storage site for TGF-β. A distinct cell surface receptor for TGF-β has been identified by cross-linking studies, and has an approximate molecular weight of about 280,000 Daltons. The biological effects of TGF-β are quite complex. The first biological effect noted was the ability of TGF-β in conjunction with either EGF or TGF-α, to stimulate fibroblast growth in soft agar, which is a phenotypic trait of transformed cells. Since then TGF-β has been shown to also inhibit both normal and transformed cell growth, possibly by lengthening the $G_1$ phase of the cell cycle, although the target cell density also appears to play an important role in the effect of TGF-β activity on the cell. TGF-β will, by itself, stimulate DNA synthesis in serum-deprived, sparse fibroblast cultures. However, TGF-β will not stimulate DNA synthesis in confluent, density arrested fibroblast cultures. The reason for the distinction has not yet been established. TGF-β will also affect EGF receptor metabolism. Short-term treatment, i.e., about 1-4 hours, of rat fibroblasts with TGF-β can decrease the number of high-affinity sites for EGF. Further treatment with TGF-β results in an overall increase in EGF receptor number for both the low and high-affinity sites. The increase in EGF receptor number by TGF-β appears to account for a synergistic response to the combination of TGF-β and EGF, as measured by DNA synthesis in the recipient cells. How these alterations in EGF receptor number are brought about, or the mechanism of synergy between TGF-β and EGF, are at present unknown.

One problem in studying the effects of PDGF, FGF, TGF-α and TGF-β on cells in culture is the difficulty in obtaining large quantities of each factor which is a typcial problem associated with proteins generated by cells as indicated above. The major storage site, in normal tissue, for these factors is the platelet. It is not only difficult to obtain large quantities of platelets for large-scale purification, but even if such quantities of platelets could be obtained, platelets presently cannot be used as a practical matter to study the biosynthesis, storage and/or release of these factors. With respect to TGF-β, it can be obtained from bovine kidney (1 kg of kidney will generally yield 3-4 micrograms of TGF-β) and FGF can be isolated in microgram levels from bovine brain or pituitary. Unfortunately, it is difficult to do biosynthetic studies in these tissues as well. Thus, the establishment of a xenograft which can synthesize these factors in generous quantities as well as provide an ample source for the genes and messenger RNAs would be very advantageous for their production and biosynthetic and physiological studies. Certain cell lines (primarily osteosarcomas) have been identified hitherto which are believed to secrete a PDGF-like molecule, Seifert, R. et al: *Nature* 311:669-781, 1984; Di Corleto, P. E. et al: *Proc. Natl. Acad. Sci. USA* 80:1919-1923, 1983; and Bowen-Pope, D. F. et al: *Proc. Natl. Acad. Sci. USA* 81:2396-2400, 1984. However, no cell lines of megakaryocytic origin, which are believed to be platelet precursors, have really been well characterized or continuously established.

The development of a megakaryocytic cell line unfortunately has proven to be very difficult. Normal human megakaryocytes can be isolated and grown in tissue culture, Kimure, H. et al, *J. Cell Phys.* 118: 87-96, 1984; Tabilo, A. et al, *EMBO J.* 3: 453-459, 1984. But generally, these cultures can only be maintained for short periods of time, and it is difficult to produce large quantities of cells. Some permanent cell lines with megakaryocytic-like features have been suggested, Tabilo, A. et al: *EMBO J.* 3:453-459, 1984; Gerwirtz, A. et al: *Blood* 60:785-789; however, these lines have been derived from patients with nonmegakaryocytic leukemias and show only limited megakaryocytic differentiation. A recent report, Morgan D. A. et al: *J. Cell. Biol.* 100:565-573, 1985, has suggested the development of human cell lines with properties similar to megakaryocytes. These lines, however, are believed to be derived from either patients with various hematologic disorders or from normal peripheral blood. They do not show the morphologic features of mature megakaryocytes though immunohistochemical studies possibly show a homogenous population of cells with megakaryoblastic features. These xenografts have been analyzed for cross-reacting material to an antibody directed against PDGF, Pantazis, P. et al: *In Cancer Cells*, Vol. 3, J. Feramiso, B. Ozanne, and C. Stiles, eds., Cold Spring Harbor laboratory, pp. 153-157, 1985. Intracellular proteins in the range of 12,000-48,000 Daltons were detected, although the mitogenic capability of these proteins has not yet been reported, nor was it reported if this cell line produced large quantities of these growth factors.

Consequently, it is therefore very desirable that a truly megakaryocytic xenograft be established and characterized in order to provide ample quantities of the growth factors, the genes and the messenger RNAs for commercial use as well as to obtain maximum information concerning the structure and synthesis of such intracellular growth promoting peptides.

SUMMARY OF THE INVENTION

In brief, the present invention alleviates the above mentioned problems and shortcomings of the present state of the art through the discovery of a novel continuous human xenograft that is morphologically similar to megakaryocytes and which is capable of producing a wide variety of proteins, including growth factors. The established xenograft was initially obtained from extramedullary soft orbital metastasis tissue biopsied from a human infant patient diagnosed as having acute megakaryoblastic leukemia and myelofibrosis. Histologically, the xenograft comprises pleomorphic cells with single convoluted nuclei or multilobed nuclei, prominent granular cytoplasm and an alveolar histologic pattern in some areas. Ultrastructurally the multilobed nuclei contain prominent nucleoli and the cytoplasmic granules contain the characteristics of granules found in megakaryocytes and platelets, which are known to be storage sites of platelet-derived growth factor. The cells are believed to be homogeneous, as about 98% of the cells stain with the appropriate antibodies specific for identifying platelets and the megakaryocytic series. For example, such cells from the xenograft are reactive for factor VIII antigen and also have GpIIb-IIIa complex antigen on their plasma membrane surfaces. Moreover, the cells of the xenograft are monophenotypic for megakaryocytes, i.e., they express markers for only megakaryocytic lineage, and they are reactive for platelet peroxidase, which is an enzyme unique to platelets and megakaryocytes. The techniques used to test for the presence of platelet peroxidase were similar to those disclosed in Breton-Gorius et al: *Blood*, 51(1):45–60 (1978).

In view of the above, and in particular the fact that the cells of the cell line have alpha-like granules in the cytoplasm, are reactive for factor VII antigen, GpIIb-IIIa complex antigen and platelet peroxidase, and are monphenotypic for only megakaryocytes, it is believed that the cell lines of the present invention are of megakaryocytic or platelet origin and have multiple marker characteristics of advanced or mature megakaryocytes. Quite amazingly, the xenograft has been successfully passaged in athymic nude mice for over a one year interval and presently exists as a stable, continuous xenograft.

A continuous xenograft in accordance with this invention has been designated CHRF-288 and is deposited with the American Type Culture Collection (ATCC) of Rockville, Md., under the Budapest Treaty accession number ATCC CRL9139. Although this indicated public availability is the simplest method of obtaining a xenograft in accordance with this invention, it is not altogether impossible or improbable that similar and functionally substantially identical human xenografts might be produced continuously by other methods in view of the teachings of this invention. Such functionally substantially identical xenografts are considered to be biologically equivalent to xenograft CHRF-288 and therefore are within the general scope of the present invention. Also, such and substantially identical xenografts, which can be obtained by those skilled in the art by modifying, cloning or subcloning the cell line described and thereby provided by the present invention, without substantially altering the morphological and functional properties of the cell line or those cultivated, are within the scope of the present invention.

The cells of the xenograft constitutively synthesize a wide variety of proteins, including several growth-like factors similar to those which are normally believed to be synthesized by platelets, such as fibroblast growth factor (FGF), and transforming growth factor-beta (TGF-$\beta$) platelet factor IV and $\beta$-thromboglobulin. Also, it is possible that the cells of the xenograft synthesize other proteins and growth-like factors, like, for instance, platelet-derived growth factor (PDGF) and transforming growth factor-alpha (TGF-$\alpha$).

The cells of the xenograft provide a continuous source of the above proteins which may or may not be naturally modified and which can be isolated by conventional ways. In addition, due to the constitutive synthesis of the proteins, the cells can provide, either directly or indirectly, a source of the genes for the proteins of interest, which by conventional genetic engineering techniques, can be introduced into, for example, acceptable microorganisms for continuous large scale production of the proteins. The cells of the xenograft can also provide an ample source of the messenger RNAs as indicated above for the proteins for the development of the cDNAs.

The above features and advantages of the present invention will be better understood with reference to the following accompanying figures, detailed description and example which are illustrative of the preferred embodiments of the present invention.

DESCRIPTION OF THE FIGURES

With reference to the accompanying figures which are illustrative of the cells of the xenograft within the scope of the invention.

DETAILED DESCRIPTION OF THE INVENTION

Figure 1:
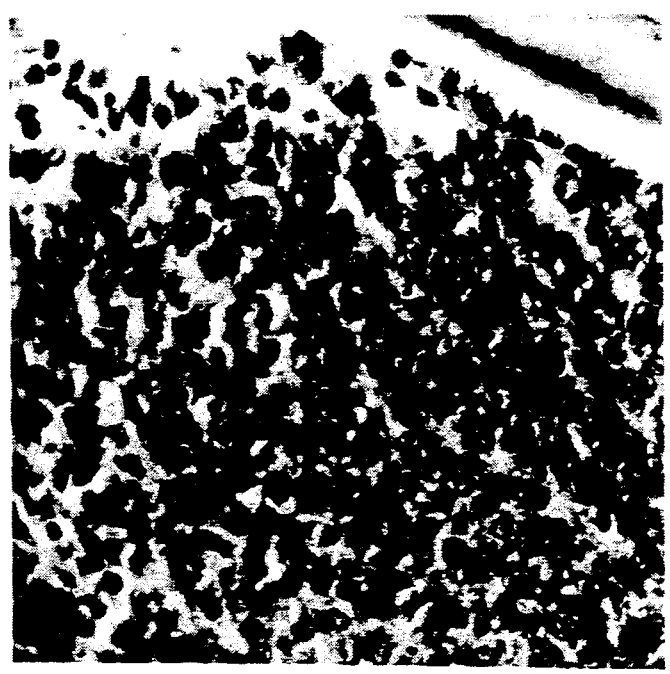
FIG. 1. Bone marrow biopsy extracted from the human infant showing replacement of the marrow by the leukemic infiltrate. The cells have pleomorphic nuclei with prominent nucleoli. Most of the nuclei are round to oval in shape though some are convoluted, and occasional multilobed nuclei are present (H&E $\times$485)

By way of illustrating and providing a more complete appreciation of the present invention and many of the attendant advantages thereof, the following detailed description is given concerning the novel continuous human megakaryocytic xenograft, methods of cultivating the xenograft, the products synthesized therefrom and methods of obtaining those products.

A novel xenograft has been established, designated as CHRF-288. The xenograft has been established from soft tissue metastasis of megakaryocytic origin. More particularly, the xenograft has been established from soft tissue metastasis of a human infant patient with acute megakaryoblastic leukemia and myelofibrosis. The cells are capable of growing in athymic nude mice for indefinite periods of time while maintaining the properties of megakaryocytes. The morphological and cytochemical features of the xenograft are characteristic of megakaryoblasts and immature megakaryocytes. Factor VIII antigen (vonWillebrand factor) is on the surfaces and in some cytoplasmic granules of the cells. Also, the cells react for platelet peroxidase and demonstrate binding reactivity with antibodies directed against components of the glycoprotein IIb-IIIa complex (such glycoproteins are presently believed to be limited to the membranes of platelets and the megakaryocytic series). Ultrastructively, the xenograft comprises a population of monophenotypic cells for megakaryocytes of variable differentiation but with constant megakaryocytic features. Numerous granules with a "bull's eye" appearance, characteristic of megakaryocytic α-granules, are present in many of the more differentiated cells. Immunoelectronmicroscopy of the xenograft demonstrates binding of the anti-factor VIII related antibody to the large, α-granules, which are believed to be responsible for the production of the PDGF-like protein and the factor VIII related antigen. No evidence of alveolar-soft past sarcoma or rhabdomyosarcoma was observed to support a finding that the cells of the xenograft of this invention were derived from those two abnormalities.

The CHRF-288 xenograft is conveniently passaged in athymic nude mice derived from NIH stock of Swiss background which are maintained in filter topped cages. With respect to the initial transplantation, a single athymic mouse, under sterile conditions in a laminar flow hood, was first anesthetized with methoxyfluorane, and delicately minced cells obtained from the soft orbital tissue mass of the human infant were transplanted subcutaneously into the mouse. The cells grew as a solid nodule in the subcutaneous tissue, measuring approximately 3.0 cm in greatest dimension. The cells were subsequently successfully passaged, at four week intervals, by delicately mincing portions extracted from the mice and reimplanting into subcutaneous tissue of other athymic nude mice. While it is presently believed that the xenograft can be cultivated in a suitable cell culture medium as well, it is considerably more difficult to do.

CASE HISTORY

A white human male infant was well until the age of 17 months when he developed generalized irritability and fever. He was first evaluated at the University of Kentucky Medical Center and had a WBC of 12,700/mm$^3$ with a normal differential, Hgb of 9.1 gm/dl, and platelet count of 22,000/mm$^3$. The direct and indirect Coombs were negative and titers to CMV and EBV were nondetectable. A bone marrow aspirate was hypocellular, with a few atypical cells. Repeat bone marrow studies including biopsy revealed myelofibrosis with scattered areas of normal hematoporesis; a few areas of undifferentiated atypical cells were noted. Chromosome analysis of the bone marrow revealed hyperdiploidy; consistent duplication of chromosomes 2,6,7,8 and 21 as well as a reciprocal 12 p:15q translocation. The Hgb F was 0.9%, LDH 786 IU, B$_{12}$ 532 ng, and serum muramidase 7 mg/ml. Additional studies included normal chest x-ray, normal abdominal ultrasound, negative skeletal survey and negative bone scan. A 24 hour urine collection for catecholamine metabolites was normal.

He was referred to Children's Hospital Medical Center in Cincinnati, Ohio at 18 months of age for further evaluation and consideration for bone marrow transplantation. A repeat blood count revealed a WBC of 21,800/mm$^3$ with 38% undifferentiated cells. The Hgb was 9.4 gm/dl and the platelet count 15,000/mm$^3$. A bone marrow aspirate showed 26% leukemic blast cells. Special stains showed blast forms to be weakly PAS positive, α-napthol esterase positive, peroxidase negative and chloracetate esterase negative. Bone marrow biopsy was 90% replaced with abnormal blast cells; no increase in reticulin fibers was noted. Radiographs demonstrated lytic lesions of the proximal humeri, as well as leukemic lines with areas of periosteal elevation. A tentative diagnosis of acute monoblastic leukemia was made.

The patient was placed on Children's Cancer Study Group protocol 213P, he was randomized to the "Denver" arm (Daunomycin 0.67 mg/kg×3 days, Ara-C 3.3 mg/kg×5 days; 6-thioguanine 1.67 mg/kg×5 days, VP16-213 5 mg/kg×2 days and dexamethazone 0.2 mg/kg/ ×5 days). Bone marrow studies on day 14 revealed a hypocellular aspirate, biopsy showed a marked reduction in the number of leukemic cells and a predominance of collagen and reticulin. Twenty-eight days after beginning chemotherapy, the patient started cycle #2 of the "Denver" regimen. Repeat bone marrow studies two weeks later demonstrated decreased marrow cellularity and continued replacement with fibrious tissue.

The patient's induction course was subsequently complicated by *Streptococcus viridans* sepsis, Pseudomonas bacteremia, Pseudomonas perirectal abscess, and Herpes Simplex Viremia.

Despite the two cycles of chemotherapy, he developed hepatosplenomegaly, progressive bony lesions and a left proptosis. CT scan of the head 8 weeks after admission revealed the latter to result from a 3 ×3 cm mass that extended from the left ethmoid sinus to the inferior aspect of the left orbit with extensive erosion of the sphenoid bones. Bone marrow studies contained increased replacement by blast cells and further increase in fibrosis Biopsy of the orbital mass demonstrated marked cytologic pleomorphism, and a nesting pattern with delicate fibrovascular septa. This pathology was suggestive of an unusual sarcoma or lymphoma. In consideration of these findings and the unsatisfactory response to prior chemotherapy, the patient was started on a chemotherapy regimen of: Vincristine 2mg/m$^2$×1 day, Actinomycin-D 15 mcg/kg/d×5 days, and cyclophosphamide 10 mg/kg×3 days (VAC). He also received 600 rads (of a planned 3000 rads) to the left orbit. Upper airway compromise due to metastatic tissue compression of the posterior cervical trachea necessitated intubation Days 62 through 85 of the hospitalization The patient had an initial response with marked decrease in the size of soft tissue masses and complete disappearance of airway compression by twenty-six days after VAC was started.

Repeat head CT scan thirty-three days after initiation of VAC therapy showed persistence of the left orbital tumor. Skeletal survey at this time demonstrated progressive bony disease. With consent of the parents, no further therapy was administered and the patient expired 3 months after admission. A postmortem examination was not obtained.

CELL TISSUE EVALUATION

With respect to an evaluation of the morphology of the cells, bone marrow aspirate smears using conventional techniques were stained with Wright stain, Sudan Black, nonspecific esterase, acid phosphatase and peroxidase. Bone marrow biopsies, i.e., bone marrow cores, were fixed briefly in $B_5$ fixative and decalcified in buffered formalin with Ca-EDTA prior to paraffin embedding and sectioning. The sections were stained with H&E, PAS, reticulin and Masson thrichrome stains using conventional techniques.

The initial bone marrow aspirates contained approximately 25% undifferentiated cells characterized by about 10 to about 30 mm diameter, round to slightly basophilic cytoplasm, azurophilic granules which were PAS positive and diastase resistant and prominent perinuclear Golgi zones. There was no reactivity with the chloracetate esterase and peroxidase stains, but α-napthol esterase stain and strong activity of the acid phosphatase stain.

The initial bone marrow biopsy showed replacement of the normal marrow by tumor cells as illustrated in FIG. 1 with oval to irregularly shaped nuclei that were variable in size and surrounded by a small to moderate amount of eosinophilic cytoplasm. Admixed with these were numerous cells with large pleomorphic, multilobulated nuclei and prominent eosinophilic, granular cytoplasm, resembling small atypical megakaryocytes. The reticulin stain showed a diffuse marked reticulin fibrosis. Initially, following the institution of chemotherapy there was a dramatic decrease in the number of leukemic cells but numerous atypical megakaryocytes persisted. Three months after beginning chemotherapy, the marrow became infiltrated by malignant cells, including cells with multilobed nuclei and prominent granular cytoplasm typical of dysplastic megakaryocytes. Many of the poorly differentiated cells and most of the well differentiated tumor cells showed strong reactivity with the PAP stain for factor VIII antigen. A postmortem bone marrow biopsy showed persistence of the leukemic infiltrate although the cellularity was markedly decreased.

Examination of the orbital tissue, initially obtained from the human infant, was conducted with light microscopy. Fresh tissue samples obtained from the orbital mass were fixed in buffered formalin, B-5 fixative or snap frozen in liquid nitrogen using conventional techniques. Paraffin embedded tissue was sectioned at a thickness of about 4μ. Frozen tissue was sectioned in a cryostat at about 4 to about 6μ. Paraffin sections were stained with hematoxylin and eosin (H&E), Periodate acid-Schiff (PAS), Jones modified Methenamine silver, Grimelius, and Wilder's reticulin method also using conventional techniques. Frozen section histochemistry for acid phosphatase, chloroacetate esterase (Leder) and nonspecific esterase activity (alpha-napthal esterase) was performed in the standard fashion.

Figure 2:
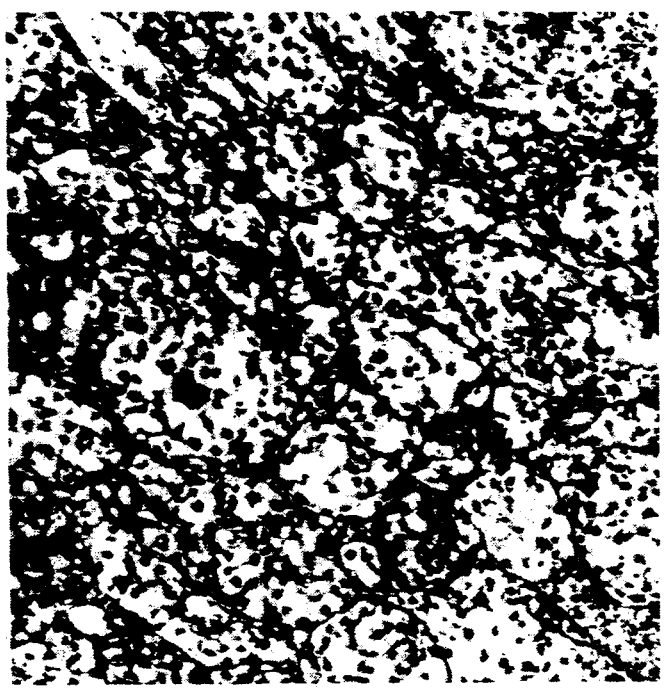
FIG. 2. Histologic appearance of orbital metastasis extracted from the infant. The tumor infiltrate has an alveolar pattern with nests of tumor cells separated by a delicate reticulin network (Reticulin $\times$150)

The orbital tissue contained malignant cells with highly pleomorphic nuclei, some convoluted and containing about 1 to about 3 prominent nucleoli. The infiltration varied, ranging from solid sheets of cells to areas with nests separated by a delicate fibrovascular septa; in occasional areas with loss of cell cohesion, there was an alveolar pattern, sharply defined in the reticulum stain as can be viewed in FIG. 2. The cytoplasm of the larger cells was granular in appearance with coarse granules that were diastase resistant and PAS positive, and with fine granules that stained with the Grimelius stain. The cells showed no chloracetate esterase or alpha-napthal esterase activity although there was strong acid phosphatase activity throughout the infiltrate. Immunohistochemistry showed strong reactivity with anti-human factor VIII antigen antibody.

Figure 3:
FIG. 3. Cells of this invention obtained from the nodular tissue removed from an athymic nude mouse. The tissue cells contain pleomorphic nuclei with prominent nucleoli. A granular chromatin pattern with clearing around prominent nucleoli is present in many of the cells. Convoluted nuclei as well as bilobed and multilobed nuclei are frequent. Tissue cells, characteristically have abundant granular cytoplasm with a prominent hof (H&E $\times$800)

With respect to the initial orbital tissue transplanted into the single mouse, it grew as a solid nodule in the subcutaneous tissue, measuring approximately 3.0 cm in greatest dimension as indicated above. The orbital tissue was successfully passaged in other nude mice. The light microscopy of the nude mouse tissue implants was very similar to that of the orbital metastasis as shown in FIG. 3 consisting almost entirely of solid sheets of cells, only occasional small blood vessels and scant fibrous stroma. An alveolar arrangement of orbital tissue cells, however, was not a component of the nude mouse tumor implants. Poorly differentiated cells, which were most numerous, had a large single round to oval nucleus, usually one large eosinophilic nucleolus and a chromatin pattern that was finely granular with some clearing around the large nucleolus. These cells had a moderately prominent amphophilic to eosinophilic granular cytoplasm with prominent perinuclear Golgi zones. Numerous mitotic figures, some atypical, were present as were necrotic cells. The better differentiated cells contained either a single large, pleomorphic, convoluted nucleus with one to two prominent eosinophilic nucleoli or multiobed nuclei with up to eight lobes, forming a ring around an abundant granular cytoplasm, bearing a striking resemblance to mature megakaryocytes.

With respect to the immunohistochemistry of the cells, several conventional assays were conducted with conventional techniques. Rabbit anti-human factor VIII antibody, swine anti-rabbit antibody and rabbit PAP reagent were obtained from Accurate Chemical and Scientific Co. (Westburg, N.Y.). Paraffin sections from the soft tissue mass and bone marrow biopsies were incubated in the anti-human factor VIII antibody at a dilution of about 1/1200 followed by swine anti-rabbit antibody at about 1/20 and rabbit PAP reagent at about 1/20 for about 30 minutes each. Peroxidase activity was detected with 3 amino 9-ethylcarbazole (Sigma). Anti-factor VIII antibody was also detected with FITC conjugated goat anti-rabbit antibody (Cappel Laboratories) at a dilution of about 1/40. Frozen sections of unfixed tumor tissue were incubated in anti-GpIIb-IIIa (T10), and anti GPIIb (Tab), monoclonal antibodies against the platelet glycoprotein IIb-IIIA complex (obtained from the University of Texas Health Science Center at San Antonio), each at a dilution of about 1/100 for about 30 minutes. Primary antibody was detected with FITC conjugated anti-mouse antibody (Miles Lab) at a dilution of about 1/40. Negative controls for the anti-factor VIII antibody consisted of tissue sections incubated in normal rabbit serum at about 1/1200, and for the T10 and Tab monoclonal antibodies, incubation in normal mouse serum at a dilution of about 1/100. OKT3, 4, 6, 8, 9, 10 and 11 were obtained from Ortho Diagnostic Systems (Raritan, N.J.). B1, B2, and J5 (cALLa) antibodies, nonimmune mouse immunoglobulin (MsIgG), and fluorescein-labeled goat anti-mouse immunoglobulin were obtained from Coulter Immunology (Hialeah, Fla.). Anti-Leu M3 was obtained from Becton-Dickinson Monoclonal Antibody Center (Mountain View, Calif.). Six-micron frozen sections attached to gelatin-coated slides and dried at room temperature for about 10 minutes were rehydrated in phosphate buffered saline (PBS) for about 5 minutes and thereafter protected from drying. Monoclonal antibodies were diluted in PBS plus 5% fetal bovine serum at concentrations deemed optimal by previous titration, and incubated with the tissue sections in a moist chamber for about 30 minutes at room temperature. Primary antibody was detected with fluorescein-labeled goat anti-mouse immunoglobulin (diluted about 1:60 in PBS) in a moist chamber for about 30 minutes at room temperature. The tissue was viewed with the 100× oil immersion objective of a Leitz Laborlux 12 fluorescent microscope. Because the tissue composition was homogeneous, antibody reactivity was readily scored as positive or negative.

Figure 4A:
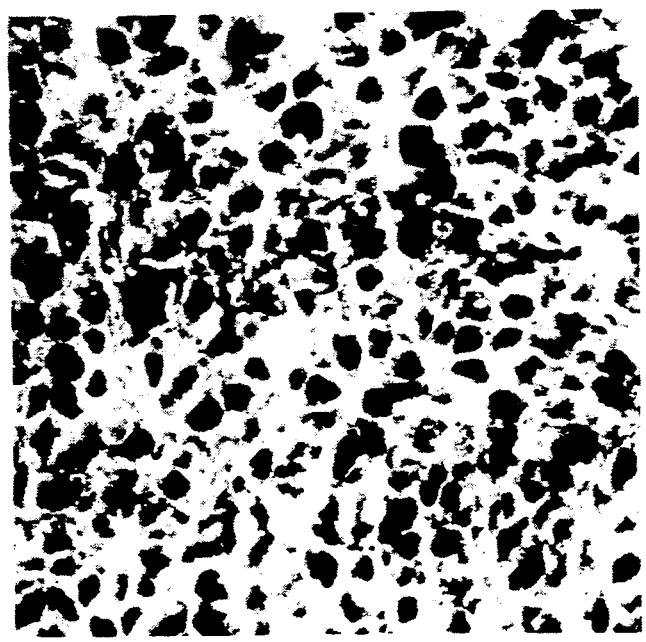
FIG. 4. Immunofluorescence of the cells of this invention obtained from the nodular tissue removed from an athymic nude mouse. Monoclonal antibodies T10 (A) and Tab (B) show a uniformly distributed, finely granular label along the plasma membrane. Antiserum to Factor VIII (C) labels most cells along the plasma membrane, with intense cytoplasmic label in occasional cells (all magnifications $\times$600)
Figure 4B:
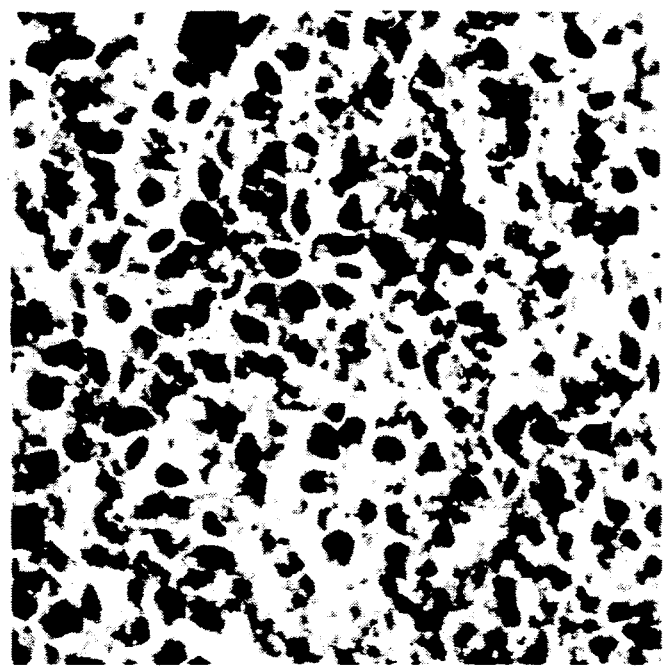
Figure 4C:

The results of histochemistry and immunohistochemistry are shown in Table I. Histochemical stains that stained the cytoplasmic granules in both the initial orbital metastasis and nude mouse tumor included the PAS, Jones and Grimelius stains. Enzyme histochemistry for acid phosphatase, chloracetate esterase and alpha-napthal esterase were negative in both the original and transplanted tumor. Factor VIII related antigen was present in both the orbital tumor and the tumor xenograft and there was labeling of the tumor cells in the nude mouse with Tab and T10 antibodies as depicted in FIG. 4. Platelet peroxidase was also present in the tumor cell. A battery of antibodies for lymphoid and hematopoetic cell surface markers including OKT3, OKT4, OKT6, OKT8, OKT10, OKT11, B1, B2, J5 (cALLa), and Leu M3 showed no labeling of the nude mouse tumor xenograft though the tumor cells did label with antibody OKT9.

TABLE I

Histochemistry and Immunohistochemistry Results

|  | Orbital Tissue | Nude Mouse Tissue |
|---|---|---|
| PAS | + | + |
| Jones | + | + |
| Grimelius | + | + |
| Acid phosphatase | + | + |
| Chloroacetate esterase | − | − |
| alpha-napthal esterase | − | − |
| anti Factor VIII related antigen | + | + |
| T10 (megakaryocytes and platelets) | ND | + |
| Tab (megakaryocytes and platelets) | ND | + |
| OKT3 (mature T-cells) | ND | − |
| OKT4 (T-cells) | ND | − |
| OKT6 (cortical thymocytes) | ND | − |
| OKT8 (T-cells) | ND | − |
| OKT9 (activated cells) | ND | + |
| OKT10 (hematopoietic stem cells) | ND | − |
| OKT11 (T-cells) | ND | − |
| B1 (B cells) | ND | − |
| B2 (intermediate B-cells) | ND | − |
| J5(cALLa) (prepre/B-cells) | ND | − |
| Leu M3 (macrophages) | ND | − |
| MsIgG (negative control) | ND | − |
| Platelet peroxidase | ND | + |

Notations in parenthesis indicate known antigen distribution.
ND - not determined
MsIgG - Mouse serum IgG For electron microscopy evaluation, fresh tissue was obtained from the nodular tissue removed from an athymic nude mouse and was diced into about 1 mm sections and immersed in 2% gluteraldehyde in cacodylate buffer (pH of about 7.14) at about 4° C. for about two hours. The tissue was then washed in cacodylate buffer and postfixed in about 1% osmium tetroxide prior to embedding in Epon. Thin sections were stained with uranyl acetate and lead citrate and examined with a Phillips 300 electron microscope. A cell suspension for immunoelectronmicroscopy was prepared from small pieces of tumor and fixed in Periodate-lysine-paraformaldehyde (PLP) fixative. After fixation for about one hour at about 4° C., cells were washed three times in about 0.1 M phosphate buffer and centrifuged in a Biofuge B microfuge (American Scientific Products) at about 2,000 rpm to form a pellet. The pellet was resuspended in peroxidase labeled rabbit anti-human factor VIII antibody diluted about 1/30 in about b 0.1 M phosphate buffer and incubated for about 1 hour at room temperature. Primary antibody was detected after about a 30 minute incubation period with diaminobenzidine substrate (20 mg DAB/10 ml of 0.05 M tris and 0.1 and 3% $H_2O_2$). Cells were then washed in about 0.1 M phosphate buffer (pH of about 7.4) and postfixed in about 1% Osmic acid in about 0.1 M phosphate buffer for about 30 minutes at room temperature. The cells were were then repelleted and dehydrated in alcohol and embedded in LX-112 (Ladd). Unstained sections were examined with the Phillips 300 transmission electron microscope. Control tissue was processed in an identical manner with exclusion of the primary antibody.

Figure 5:
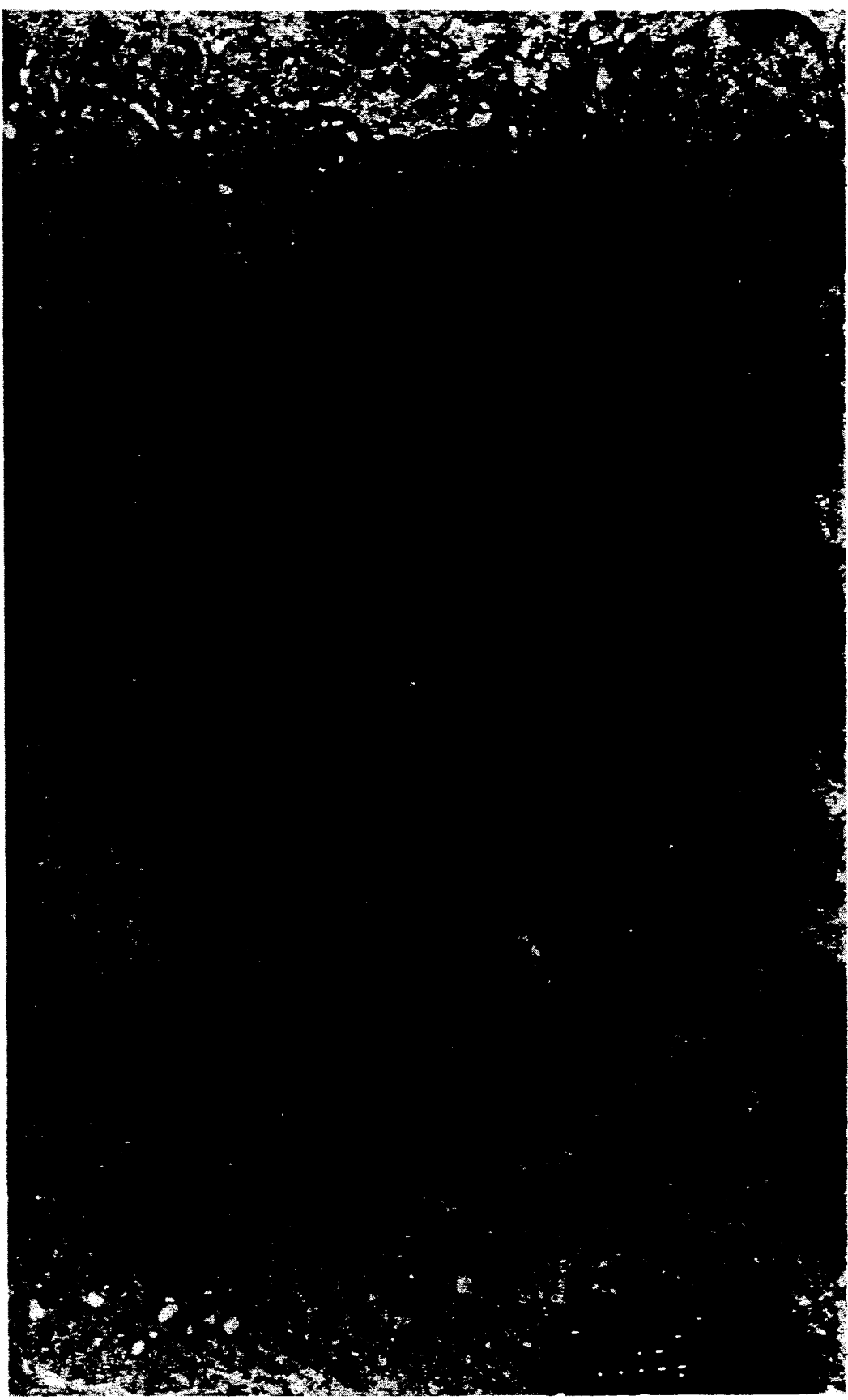
FIG. 5. Electron micrograph of cells of this invention obtained from the nodular tissue removed from an athymic nude mouse. Low magnification of a large tissue cell of this invention with a multilobed nucleus, prominent nucleoli and some condensation of chromatin along the nuclear membrane. The cytoplasm contains numerous granules of variable size and electron density, large Golgi complexes and numerous vesicles and tubular channels in the peripheral cytoplasm ($\times$4950)
Figure 6:
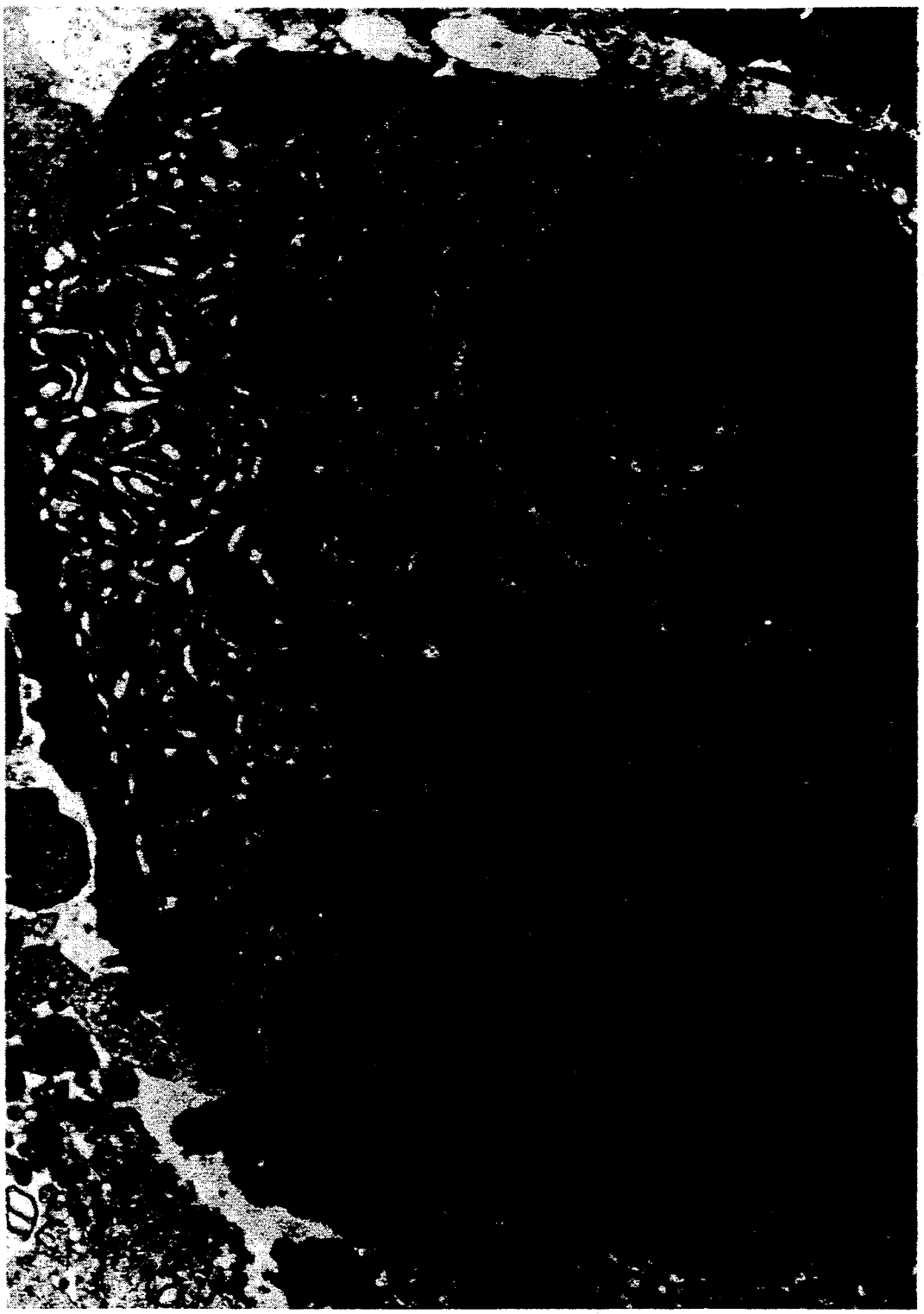
FIG. 6. Higher magnification of cells of this invention obtained from the nodular tissue removed from an athymic nude mouse showing a complex network of demarcation-like channels in the cytoplasm. Note the rim or organelle poor cytoplasm in the marginal zone ($\times$10,800)
Figure 7A:
FIG. 7. A, top. Cells of this invention obtained from the nodular tissue removed from an athymic nude mouse containing numerous granules of variable size and electron density. The smaller granules contain a central electron dense core ("bull's eye") characteristic of α-granules (double arrow). Larger granules (single arrow) with more coarsely granular content and variable electron density are also present. (x15,000) B, bottom. Detail of larger granular in A showing granular matrix and central electron dense core (×25,000)
Figure 7B:
Figure 8:
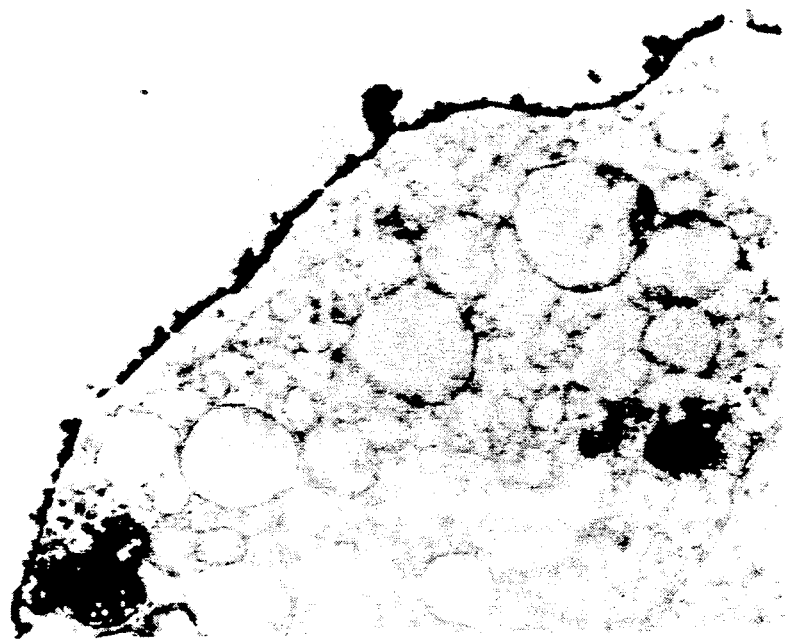
FIG. 8. Immunoelectronmicrograph of cells of this invention obtained from the nodular tissue removed from an athymic nude mouse labeled with anti-factor VIII antibody. A dense layer of peroxidase reaction product is seen on the cell membrane surface and in a large cytoplasmic granule corresponding to the larger granules in FIG. 7 (×20,000)

Ultrastructurally the cells contained single convoluted or multilobed nuclei with prominent nucleoli and a thin rim of condensed nucleoprotein along the nuclear membrane as viewed in FIG. 5. The cytoplasmic margins were distinct with occasional interdigitating cell processes along the abutting surfaces of adjacent tumor cells. In the more poorly differentiated cells the cytoplasma was nondescript with numerous free ribosomes, polyribosomes, a small to moderate amount of rough endoplasmic reticulum (RER) and relatively sparse granules. The more differentiated cells had a complex division of the ctyoplasm into three distinct zones. The first zone, a perinuclear zone, contained numerous ribiosomes, profiles of RER, small and large granules, large Golgi apparatus, a few round to oval mitochondria with straight, thin tubular cristae and occasional centrioles. The second zone, an intermediate zone, contained numerous mitochondria, particulate glycogen, numerous polyribosomes and relatively frequent granules which varied in size and appearance. The cytoplasm in some cells was pervaded by a system of vessicles and tubules in the outer portion of this zone, suggestive of developing demarcation channels as shown in FIG. 6. The granules differed in size, shape, internal content and presence of a central dense nucleoid. Numerous small granules with an electron dense core surrounded by material of lesser density as depicted in FIG. 7 were present and appeared to bud from the Golgi apparatus. Larger membrane bound granules with either finely granular contents or more dense coarsely granular material were also present, some of which had a central dense core as observed in FIG. 8. And, a rim of condensed organelle poor cytoplasm formed the marginal third zone in the most differentiated cells, but no budding platelets were identified. Immunohistochemistry for localization of factor VIII antigen at the ultrastructural level showed dense labeling of the cell surface in addition to labelling of the larger cytoplasmic granules as can be seen in FIG. 8.

Products of the Cell Line

The CHRF-288 xenograft is unique in generating many of the products known to be elaborated by platelets. The CHRF-288 xenograft constitutively produces a wide variety of proteins having different physiological activities in isolatable amounts. Thus, the CHRF-288 xenograft provides a method for the production of a large number of polypeptides of physiologic interest. In addition, because of the constitutive production of these polypeptides, the CHRF-288 xenograft, due to its continuous cultivation, makes available the genes and the messenger RNAs for these polypeptides in relatively large amounts. By employing conventional techniques, the genes and messenger RNAs for the desired polypeptides may be separated from the mass of genese and messenger RNAs present. Once isolated, the selected genes can be used to transform microorganisms for production of such polypeptides, and the selected messenger RNAs can be used for production of cDNAS.

The describing the various products produced by the CHRF-288, the direct production, isolation and purification of the polypeptides by the CHRF-288 xenograft will be described. This will then be followed by the example which concerns a description of the extraction of the initial cells from the orbital tissue of the human infant patient and the continuous cultivation of those cells in athymic nude mice to generate the stable continuous CHRF-b 288 xenograft.

Tumors were grown in athymic nude mice, surgically removed, and then homogenized either in a neutral pH buffer (about 10 mM sodium phosphate, about 80 mM NaCl, about pH 7.4) or about 0.1N acetic acid. The resulting extract was then clarified by centrifugation and the pellet reextracted two times with about 1.0 M NaCl (this is modeled after the procedure of Ross et al for the purification of PDGF, Raines, E. W. et al: *Method in Enzymology* 109:749-773, 1985). The combined supernatants were then dialyzed against a low salt (0.08 M NaCl) buffer and the extract clarified by centrifugation. The growth factor activity found under acidic homogenization conditions has been tentatively identified as PDGF-like by its ability to stimulate DNA synthesis in quiescent 3T3 cells, its stability at about 100° C., and its loss of activity, at about 100° C., in the presence of mercaptoethanol (Table 2).

TABLE 2

| Sensitivity of Acid-Extracted Material to Mercaptoethanol | | |
|---|---|---|
| Sample | | [$^3$H]-dThd Incorporated (cpm) |
| Expt. I | Control | 4,352 |
| | +12.5 μg extract | 20,946 |
| | +12.5 μg (htd) | 23,019 |
| Expt. II | Control | 1,816 |
| | +18.75 μg (dialyzed) | 19,261 |
| | +18.75 μg (htd,+MSH) | 6,968 |

A sample of acid extracted tumor (5 mg/ml) was diluted 1:20 in 10 mM Tris, 150 mM NaCl, pH 7.4 and heated at 100° C. for 5 minutes with or without 0.7% mercaptoethanol (MSH). Samples containing MSH were dialyzed against PBS before being used in the assay. Either 50 μl (Expt. I) or 75 μl of extract were tested in each experiment. Mitogenic activity was assayed as described herein. Briefly, serum-deprived 3T3 (Swiss) cells were stimulated by the addition of growth factor, and then 16-20 hours post addition the cells were pulsed with [$^3$H]-thymidine (dThd). Data are expressed as trichloroacetic acid precipitable counts per minute.

Figure 9:
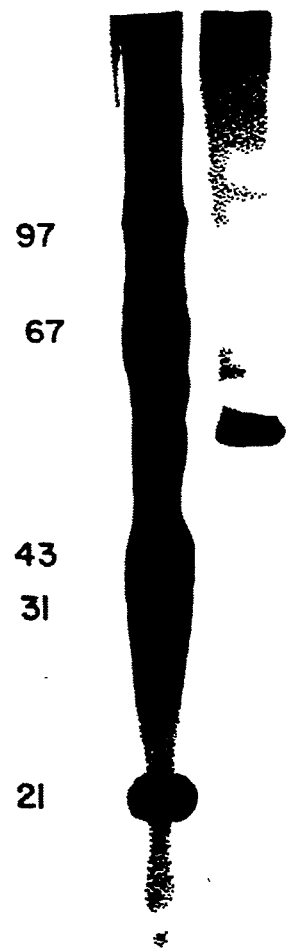
FIG. 9. Analysis of Affi-gel Blue purified platelet-derived growth like-factor generated by cells of this inention obtained from the nodular tissue removed from an athymic nude mouse on a 10% SDS-PAGE gel. Approximately 2 μg of material were run on the gel (in the absence of mercaptoethanol) and the gel was then silver stained. The molecular weight standards are, from the top 97K, 67K, 43K, 31K and 21.5K. A major band is present at approximately 56K, and several other minor bands are present in the 30K region.

The material extracted at neutral pH has been further purified by binding to CM-Sephadex and growth factor activity was eluted, in batch technique, with 0.5 M NaCl. Over 250,000 units (2 units of activity are equivalent to the mitogenic response of 5% calf serum) of growth factor activity were recovered at this step after starting with about 65 grams of tumor. The CM-Sephadex purified material has also been passed through an Affi-gel Blue column, and growth factor activity was eluted from the column with about 50% ethylene glycol, about 1.0 M NaCl. This material appears to be similar to basic FGF as it is heat and acid sensitive (Table 3), and will also down-regulate and EGF receptor (Table 4). FGF is believed to down-regulate the EGF receptor which is also a property of PDGF, Bowen-Pope, D. F. et al: *J. Biol. Chem* 257:5161-5171, 1982; Nishimura, J., et al: *Proc. Natl. Acad. Sci USA* 79:4303-4307, 1982. Heat inactivated extract did not down-regulate the receptor (Table 4). This material contains 1 unit of activity per 35 ng of protein (Table 5), and consists mainly of two major bands on a silver stained gel (FIG. 9). One of these bands is at about 56,000 Daltons; the others are in the range of about 30,000 Daltons. Co-incubation of the extract with $^{125}$I-EGF, at about 4° C., acid not inhibit EGF binding, nor was any cross-reacting material to an anti-EGF antibody found in the megakaryocyte extract. In addition, a 3T3 cell variant lacking EGF receptors responds to the extract, indicating that EGF is not the primary mitogen. This puts an upper limit on possible EGF contamination of the extract at about 0.1 ng/ml. This material also contains proteins which will cross-react, in an ELISA, with monoclonal antibodies directed against the amino terminal region of the v-sis peptide (obtained from the Scripps Institute) (Table 6), indicating that a PDGF-like molecule (in terms of structure, not heat and acid sensitivities) may also be present in this extract. The above results suggest that both a PDGF-like, and possibly an FGF-like activity, are generated by the xenograft. Over 4,000 units of growth factor activity are believed to be present per gram of tumor, indicating that sufficient material is present for purification (15 grams of tumor can be obtained per mouse). To compare this to platelets, 3 units of outdated platelets also contain about 4000 units of growth factor activity after the CM-Sephadex step, indicating that the xenograft is truly an ample source for the growth-like factors. The data presented in Table 5 indicates that after utilizing the Affi-gel Blue column 1 unit of growth factor activity corresponds to 36 ng of material, and only a few protein bands are seen on an SDS-silver stained gel (FIG. 9).

TABLE 3

| HEAT AND ACID SENSITIVITY OF NEUTRAL pH TUMOR EXTRACT | |
|---|---|
| Sample | [$^3$H] cmp Incorporated |
| Control | 22,865 |
| + extract | 222,196 |
| + heated extract | 19,211 |
| + acid-treated extract | 75,250 |

Tumor was extracted at neutral pH and purified through the Affi-gel Blue column. Approximately 4 units of activity (140 ng) were tested, in the presence of 1 mg/ml BSA. Heating consisted of placing the sample in a boiling water bath for 5 minutes. Acid treated samples were microdialyzed against 1.0M NH$_4$Ac, pH 3.5 and then left at pH 3.5 (4° C.) for 48 hours (shorter treatments reduce activity to a smaller extent). The sample was then microdialyzed again to raise the pH to 7.4, and tested for mitogenic activity, as described in the legend to Table 2.

TABLE 4

DOWN-REGULATION OF THE EGF RECEPTOR BY THE MEGAKARYOCYTIC EXTRACT

| Sample | % Control Binding |
|---|---|
| No addition | 100 |
| + crude PDGF | 63 |
| + tumor extract | 48 |
| + EGF | 52 |
| + heated tumor extract | 105 |

EGF binding was measured at a concentration of 5 ng/ml [$^{125}$I]-EGF for 4 hours at 4° C. Non-specific binding was assayed in the presence of 500 ng/ml EGF, and was 10% of the total binding measured. Swiss 3T3 cells (at a density of $3 \times 10^4$ cells/cm$^2$) were pre-incubated with the samples to be tested for 2 hours at 37° C. prior to initiating the binding assay. All experiments were done in 35 nm dishes, and 4 units of crude PDGF were added (purified through the CM-Sephadex step), 10 units of Affi-gel Blue purified tumor extract (heated tumor was treated at 100° for 5 minutes) were tested, as was 1 ng/ml EGF. Control binding was 2624 cpm; the [$^{125}$I]-EGF had a specific activity of 30 Ci/μg. All points are the average of duplicate determinations, with a standard deviation of less than 7%.

TABLE 5

PURIFICATION OF GROWTH PROMOTING ACTIVITY FROM THE TUMOR LINE

| Sample | Total Units | Specific Activity (Units/μg Protein) | Total Protein (mg) |
|---|---|---|---|
| Crude extract | $8.6 \times 10^5$ | 0.11 | 7869 |
| CM-Sephadex (0.5M eluate) | $2.0 \times 10^5$ | 2.63 | 76 |
| Affi-gel Blue eluate | $4.0 \times 10^5$ | 27.8 | 14 |

Data are taken from a purification starting with 50 grams of tumor. Columns were run as described in the text. Note that running the Affi-gel Blue column results in an activation of mitogenic activity as compared to the CM-Sephadex eluate. Activities of fractions were determined by assaying various dilutions of fractions and determining the point at which 50% of the stimulation brought about 5% calf serum was reached. This point is defined as 1 unit of growth factor activity. All growth dilutions were done in DME/BSA (1 mg/ml).

TABLE 6

ELISA RESULTS USING ANTI-v-sis MONOCLONAL ANTIBODIES

| Sample (antigen) | Monoclonal Antibody | Absorbance 410 nm |
|---|---|---|
| SSV cell lysate | #1, 1/100 | .661 |
|  | #2, 1/100 | .605 |
| Megakaryocyte extract | #1, 1/100 | .556 |
|  | #1, 1/1000 | .387 |
|  | #2, 1/100 | .790 |
|  | #2, 1/1000 | .637 |

Antigen was prebound to a flexible 96 well plate for 18 hours 4° C. After washing appropriate dilutions of two monclonal antibodies directed against the amino terminal end of the v-sis product (which is present in PDGF) were incubated with the dish, and then a second antibody, goat anti-mouse conjugated with β-galactosidase, was added. β-galactosidase activity was then assayed and the absorbance at 410 nm determined. Background levels of β-galactosidase were also determined using BSA as the antigen, and those values (.230 for 1/100 dilution; .100 for a 1/1000 dilution) are substracted from the values given above. The sample of megakaryocytic extract used was purified through the CM-Sephadex and Affi-gel Blue columns (1 unit is equivalent to 36 ng of material); an SSV-cell lysate was prepared by sonication (5 seconds) of SSV transformed 3T3 cells, which were obtained from the NIH.

Figure 10:
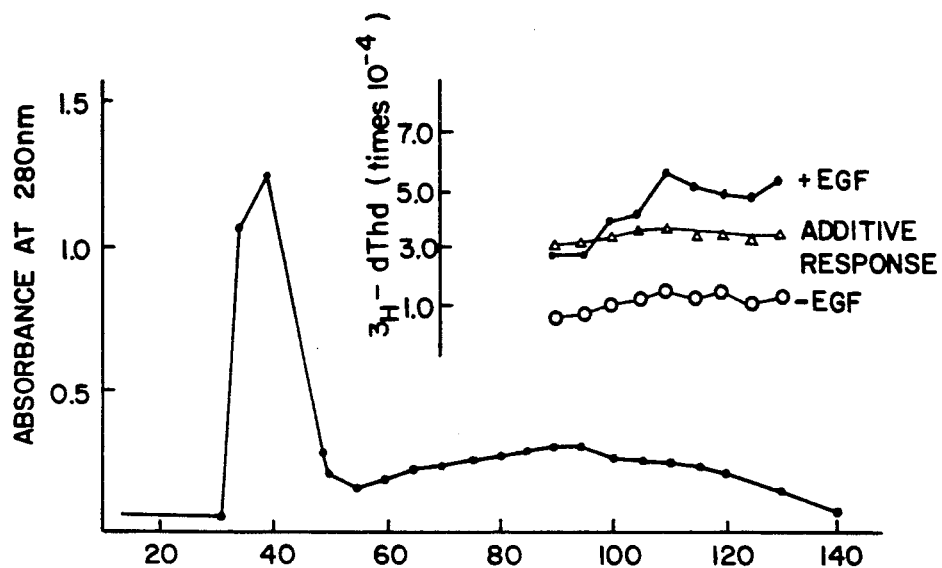
FIG. 10: P-60 chromatography of an acidic/ethanol extract of protein fractions derived from cells of this invention obtained from the nodular tissue removed from an athymic nude mouse which did not bind to CM-Sephadex. Material from 40 grams of tumor were treated as described herein and run through a 2.5×95 cm column of P-60 in 1.0N acetic acid. The column was run at 5 mls/h, and fractions of 3 ml were collected. Aliquots of various column fractions were then microdialyzed, in the presence of 100 μg BSA, against 4 mM HCl, and the resulting material then utilized for the following bioassays. The first was growth in soft agar in the presence of EGF and the positive fractions are indicated by the solid bar. The second assay was to determine if various fractions could synergistically enhance the mitogenic effect of EGF (2.5 ng/ml). The inset demonstrates the results and shows a clear enhancement of the additive response for fractions 110-140. EGF induced mitogenesis gave 37,000 cpm; background (no stimulation) was 11,000 cpm, and is subtracted from all values. For this experiment TGF-β containing samples were preincubated with quiescent NRK cells for 8 hours before adding EGF and 10 μl of each fraction was tested. DNA synthesis was then assayed 16-20 hours post EGF addition.

In addition to the growth-like factor activity, both TGF-α and β-like activities are believed to be found in the protein fraction which did not bind to the CM-Sephadex column (which is run at pH of about 7.4). These fractions were concentrated by Amicon ultrafiltration, dialyzed against about 1.0 N acetic acid, and lyophilized. The residue thus obtained was then extracted with an acidic ethanol solution and the supernatant fraction retained. Protein was then precipitated from these fractions by the addition of ethanol and ether, and the precipitate was redissolved in about 1.0 M acetic acid. Aliquots of this fraction would compete with EGF for binding to the EGF receptor (Table 7), indicating that TGF-α is present. Chromatography of the resulting extract in about 1.0 N acetic acid on a P-60 column, allowed the demonstration of TGF-β activity. TGF-β activity can be shown by the following assays; fractions containing TGF-β synergistically enhanced the EGF (2.5 ng/ml) induced mitogenesis of a rat fibroblast (NRK) cell line (FIG. 10); pre-incubation of the NRK cell line with the same column fractions reduced [$^{125}$I]-EGF binding to the high affinity EGF receptor; and finally, these same fractions also are believed to stimulate NRK cell growth in soft agar in the presence of EGF at 2.5 ng/ml. In addition, a crude extract for TGF-β content (utilizing a radioreceptor assay) was assayed and cross-reactivity was shown at a level indicating that about 1 to about 2.5 μg TGF-β is present per gram of tumor.

TABLE 7

THE PRESENCE OF TGF-α IN THE MEGAKARYOCYTIC EXTRACT

| Sample | [$^{125}$I]-EGF Bound, cpm/dish |
|---|---|
| Control | 2998 (100%) |
| + Extract | 2088 (70%) |

[$^{125}$I]-EGF (5 ng/ml) binding was assayed on confluent NRK cell monolayers as desribed in the legend to Table 4. Thirty μg (20 μl) of ether/ethanol precipitated extract was added to the cells simultaneously with the iodinated growth factor, and binding allowed to occur for 4 hours at 4° C. Binding assays were done in triplicate with total binding at 3510 ± 82, non-specific binding at 511 ± 36, and in the presence of extract 2599 ± 180.

Figure 11:
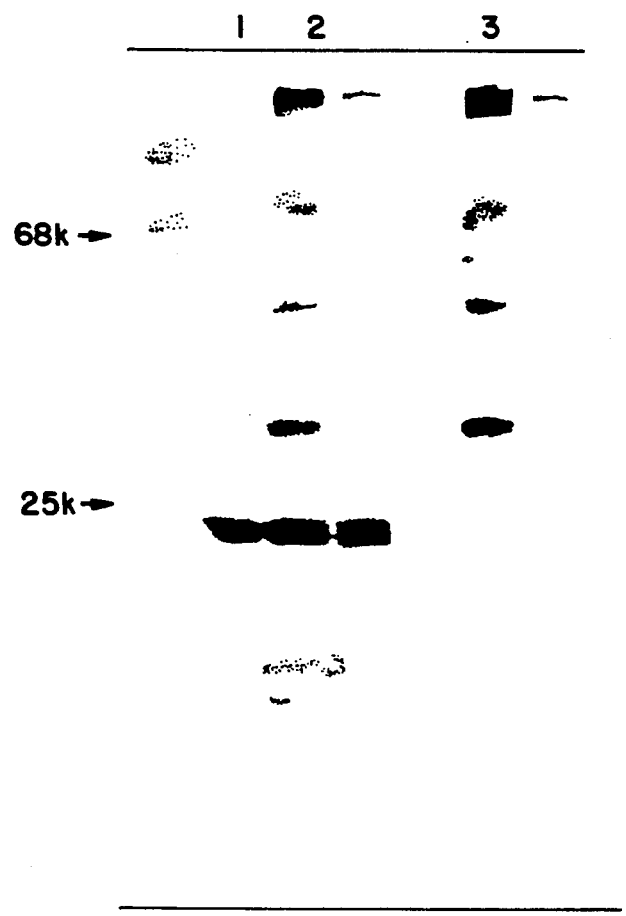
FIG. 11. Western blot analysis of an acidic ethanol extract of the megakaryocytic xenograft of this invention obtained from the nodular tissue removed from an athymic nude mouse. Samples were run on 10% SDS-polyacrylamide gels and electroblotted to nitrocellulose. The nitrocellulose was blocked with BSA and incubated overnight with affinity purified antibodies to either TGF-β or EGF. After washing, the membranes were incubated with gold-labeled goat anti-rabbit IgG and were then subjected to a silver enhancement procedure for intensifying the bands. The only major band which appears to be specific migrates with human platelet TGF-β. Lanes 1 and 3 contain 10 ng platelet TGF-β; Lanes 2 and 4 30 ng equivalents (based on inhibition of [$^{125}$I]-TGF-β binding) of an acidic ethanol extract of the tumor line. Lanes 1-3 were treated with anti-TGF-β; Lane 4, with anti-EGF. The anti-EGF antibody does not cross react with TGF-α.
Figure 12:
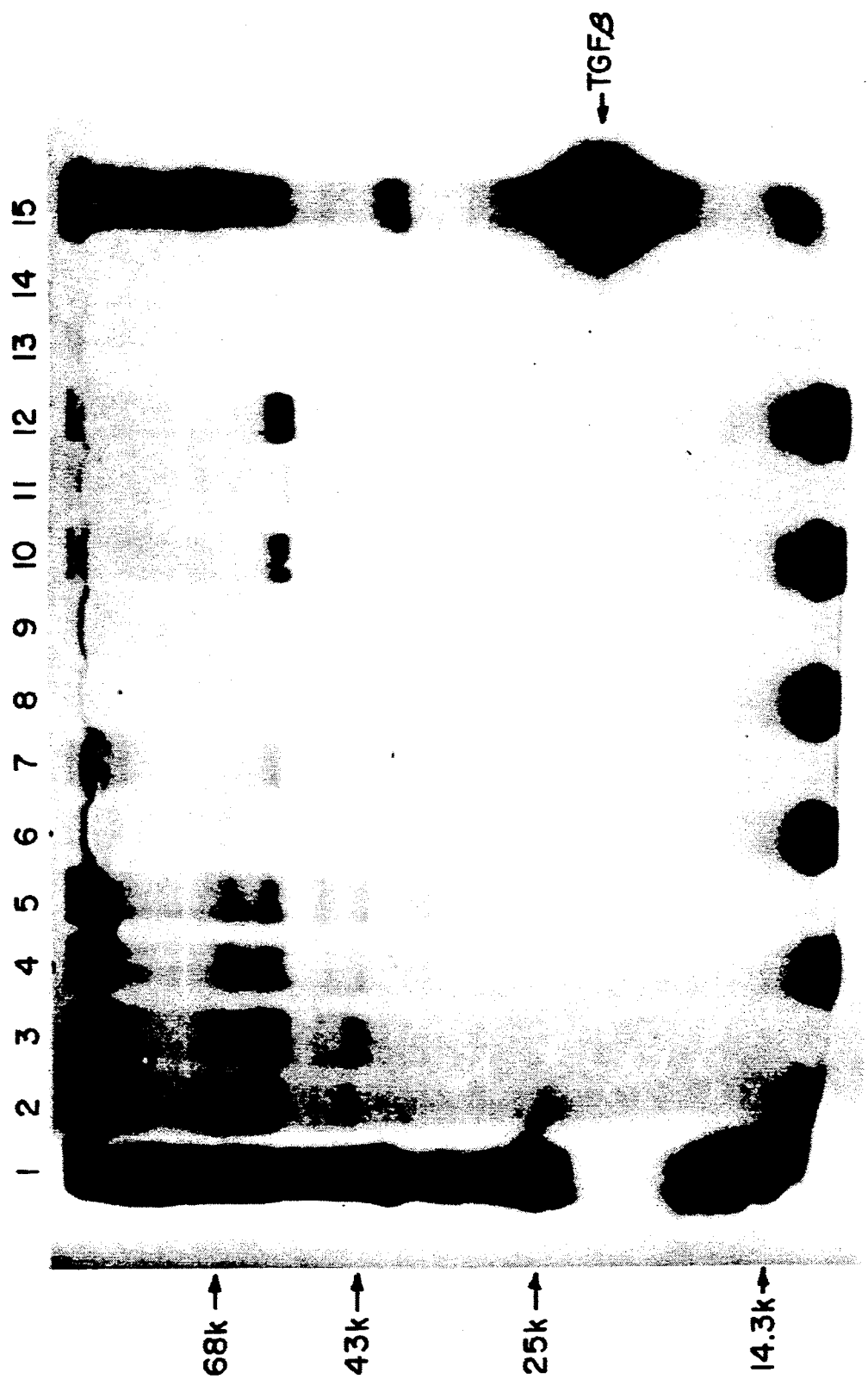
FIG. 12. An autoradiogram of immunoprecipitated, [$^{35}$S]-labeled tissue extracts of this invention obtained from the nodular tissue removed from an athymic nude mouse. Tumor nodules were excised from the mouse dissociated into a single cells suspension using both trypsin and mechanical disruption. One million cells were plated per 35 mm dish in DME containing 10% the normal levels of methionine and cysteine and 2% dialyzed calf serum. After a one hour incubation at 37° 500 μC$_i$ of [$^{35}$S]-methionine and 500 μC$_i$ of [$^{35}$S]-cysteine were added to each dish, and the cells were harvested either after 3 or 24 hours of labeling. The following samples were utilized for the immunoprecipitations: the media bathing the cells, an acidic ethanol extract of sonicated cell pellets, and the detergent solubilized pellet from the non-soluble material in acidic ethanol. An equal number of TCA precipitable counts (50,000) was then utilized for all immunoprecipitation, using either anti-TGF-β or normal rabbit serum. Immune complexes were pelleted using insoluble protein A and the complexes removed from the carrier by boiling the presence of SDS. The samples were then run on 10% SDS-acrylamide gels, enhanced, dried, and exposed. This figure is a 10 day exposure at −80° C. Lanes 2 and 3 contain the media from cells harvested at 3 hours; lanes 4,5 the 24 hour media; lanes 6,7 the 3 hour acidic ethanol extract; lanes 8,9 the 24 hour acidic ethanol extract; lanes 10,11 the 3 hour detergent solubilized pellet; lanes 12,13 the 24 hour solublized pellet; and lane 15 [$^{125}$I]-TGF-β. Even number lanes were immunoprecipitated with anti-TGF-β; odd number lanes with normal rabbit serum.

Turning to FIG. 11, this Figure shows a Western blot of an acidic ethanol extract of the megakaryocytic xenograft of this invention obtained from a nodular tissue removed from an athymic mouse. As can be seen in FIG. 11, the major specific band visualized was at about 25,000 Daltons, running what is believed to be identical to platelet TGF-β. The data in FIG. 12 is believed to demonstrate radiolabeling of the tumor line and immunoprecipitation of the TGF-β precursors. After about a three hour labeling period with both [$^{35}$S]-methionine and [$^{35}$S]-cysteine, both about a 12,500 and about a 60–70,000 Dalton species are immunoprecipitated by the antibody to TGF-β. In particular, the 60–70,000 Dalton species may not be soluble in acidic ethanol, as it is found primarily in the pellet following acidic ethanol treatment of the cells. These bands are not seen using normal rabbit serum. These may represent the monomer and precursor, respectively.

Since pulse-chase experiments may be utilized to study the biosynthesis of these growth-like factors, preliminary studies can be performed to determine if tumor cell suspensions will show significant protein labeling with [$^{35}$S]-methionine. A tumor nodule can be dissected from a mouse and minced in methionine-free Dulbecco's medium (supplemented with about 10% dialyzed calf serum) to which trypsin can be added to a final concentration of about 0.02%. The tumor fragments can then be further minced until a cell suspension is obtained and transferred to a centrifuge tube. After washing with medium, the cells can be transferred to 35 mm petri dishes. To each dish, at about $4.2 \times 10^5$ cells per milliliter, either 25, 50 or 100 microcurie of [$^{35}$S]-methionine can be added and incubated at about 37° C. for various time intervals. The [$^{35}$S]-methionine uptake can be determined from trichloracetic acid precipitate counts. After a slight lag, uptake is believed to be linear up to three hours after culturing the cells (Table 8) and proportional to the amount of [$^{35}$S]-methionine added to the media. Cells also are believed to remain viable for about 48 hours under these conditions (as determined by trypan blue exclusion).

It should be thus apparent to those skilled in the art, that this unique xenograft of megakaryocytic origin, which can be cultivated continuously and in large quantities, contains many growth-like factor activities similar to those presently found in platelets.

TABLE 8

[$^{35}$S]-METHIONINE INCORPORATION INTO DISSOCIATED TISSUE CELLS

| Labeling Conditions | Time of Labeling (h) | cpm Incorporated/cell |
|---|---|---|
| [$^{35}$S]-met at 25 μCi/ml | 1 | 0.35 |
|  | 2 | 0.93 |
|  | 3 | 1.87 |
| [$^{35}$S]-met at 50 μCi/ml | 1 | 0.63 |
|  | 2 | 1.80 |
|  | 3 | 3.43 |
| [$^{35}$S]-met at 100 μCi/ml | 1 | 1.10 |
|  | 2 | 3.50 |
|  | 3 | 7.67 |

Cells from a single tissue module were dissociated with trypsin and plated at 4.2 × 10$^5$ cells per 35 mm dish (1 ml/dish) in Dulbecco's modified Eagle's medium (methionine free) supplemented with 10% dialyzed calf serum and the indicated amount of labeled methionine. At the indicated times an aliquot of cells (200 μl) was removed from the dish and trichloracetic acid precipitable counts determined.

Purification of the Growth-Like Factors Present in the Megakaryocytic Tumor Line A. General Assays That Can Be Utilized Growth factor activity (both PDGF-like and FGF-like) may be assayed, for instance, by utilizing the following two procedures. The first is a measurement of DNA synthesis in quiescent cells stimulated to enter the cycle by addition of growth factors. Raines et al: *Methods in Enzymology* 109;749-773, 1985 have described this procedure in detail. This assay consists of plating out 3T3 cells in multiwell dishes (either 24 or 48 wells/dish) and, after growth for 10 48-72 hours such that the cells are only one doubling from confluency, depleting the cells of serum by changing the media to 0.5% calf serum. After an additional 72 hours, the cells are quiescent. Putative growth factors are then added and 16-20 hours later the cells are pulsed with [$^3$H]-thymidine. Trichloroacetic acid precipitable counts are determined, and all samples are compared to the stimulation brought about by 5% calf serum. A unit of growth factor activity can be defined. The second method for assaying PDGF is to incubate 3T3 cells with putative PDGF containing column fractions, and then to assay EGF binding to the cells. PDGF will down-regulate the EGF receptor and this assay can be useful for confirming the results of the DNA synthesis assay outlined above. However, one must be cautious in utilizing this assay as factors other than PDGF (such as FDGF and TGF-β) will also down-regulate the EGF receptor. FGF is believed to down-regulate the EGF receptor. PDGF-like activity can be distinguished from basic FGF-like activity by both acid sensitivity (1.0 N acetic acid), heat sensitivity (FGF is sensitive to both heat and acid), and response by target cells (specifically vascular endothelium).

TGF-α can be assayed on the basis of its binding to the EGF receptor. TGF-α normally competes with EGF for binding to the EGF receptor, so a reduction in binding is expected when the sample is co-incubated with EGF. Both A431 (a human epidermal carcinoma cell line with an unusually high number of EGF receptors) and NRK cells are suitable for use in this assay. Pre-incubation of the cells with TGF-α is also believed to down-regulate the EGF receptor, thus also leading to reduced EGF binding. TGF-α can also be assayed by enhancing the growth of NRK in soft agar in the presence of TGF-β, Assoian, R. K. et al: In *Cancer Cells*, Vol. 3, J. Feramiso, B. Ozanne and C. Stiles, eds., Cold Spring Harbor Laboratory, pp. 59-64, 1985. Whereas the reduction in EGF binding is believed to be the fastest and easiest screen, the soft agar assay can also be utilized to confirm to the EGF assay results (TGF-β can be purified from platelets for use as a positive control in this assay). EGF binding can be done as previously described, Lieberman, M. A. et al: *Biochem. Biophys. Res. Commun.* 92:696-702, 1980, utilizing purified EGF purified by the standard procedures, Savage, Jr., C. R. et al: *J. Biol. Chem.* 247:7609-7611, 1972. Iodinations can be performed utilizing enzymobeads, *Biochem. Biophys. Res. Commun.* 92:696-702, 1980, and non-specific binding can be assayed utilizing a 100-fold excess of non-labeled EGF. Binding assays can be done for about 4 hours at about 4° C. with two concentrations of EGF (2.5 ng/ml and 20 ng/ml) such that both high-affinity and low affinity sites can be examined.

TGF-β is believed to be best assayed by its ability to stimulate the growth of NRK cells in soft agar, in the press EGF, Assoian, R. K. et al: *J. Biol. Chem.* 258:7155-7160, 1983. TGF-β can also be assayed by down-regulating the high-affinity site of the EGF receptor, Assoian, R. K.: *J. Biol. Chem.* 260:9613-9617, 1985 and Massague, J.: *J. Cell. Biol.* 100:1508-1514, 1985, as described for PDGF. TGF-β is believed to not compete for binding to the EGF receptor, so this can distinguish it from TGF-α. TGF-β can also be assayed by synergistically enhancing the rate of DNA synthesis in EGF treated cells, *J. Biol. Chem.* 260:9613-9617, 1985. In this assay, NRK cells can be pretreated for about eight hours with TGF-β, and then EGF (2.5 ng/ml) is added. DNA synethesis is assayed for about 16-20 hours after EGF addition, and a synergistic response can be observed if TGF-β is present (See FIG. 10). Another rapid assay that can be utilized is to examine the inhibition of cell growth, by TGF-β, of a cell line which is sensitive to TGF-β. A549 cells, Roberts, A. B. et al: *Proc. Natl. Acad. Sci. USA* 82:119-123, 1985, fit into this category. To exponentially growing A459 cells various TGF-β containing samples can be added, and about 18-20 hours later, a [$^3$H]-thymidine pulse can be done. TGF-β should inhibit A549 growth, and this should be reflected in a reduced incorporation of [$^3$H]-thymidine. The presently believed most reliable assay for TGF-β however, is the soft agar response. This assay is time consuming, however, and it generally takes at least a week before any results can be obtained. Thus, mitogenesis assays can be utilized as quick screens but all results should be confirmed with the soft agar assay. Colony growth in soft agar can be quantitated by using a Magiscan image analysis computer which can count the number of colonies greater in area than about 6,000 μm$^2$ in about a 5 cm$^2$ portion of a 35 mm dish. Such a device is available in our Department and optimal conditions have been established.

B) Purification Techniques That Can Be Utilized

Both PDGF and TGF-β have been purified to homogeneity from outdated platelets, and FGF from bovine bran, Gospodarowicz, D. et al: *Proc. Natl. Acad. Sci. USA* 81:6963-6967, 1984, and purification can follow those procedures. Tumor extracts can be prepared by extraction at neutral pH as previously described and PDGF and FGF-like factors separated from the TGF α and β by chromatography on CM-cellulose. Growth factor-like activity can then be passed through, and eluted from the Affi-gel Blue column. Further purification can then be obtained by trying gel filtration (G-75), affinity chromatography (heparin-sepharose) or hydrophobic chromatography (phenyl sepharose), *Methods in Enzymology* 109:749-773, 1985. If after all these steps the material is not yet pure, the following steps can be utilized: non-denaturing gel electrophoresis, Antoniades, H. N.: *Proc Natl Acad. Sci. USA* 78:7314-7318, 1981, (amazingly, Coomassie-blue stained PDGF can be cut out of the gel, eluted from the gel, and still retains activity) may yield a sizable purification, and isoelectric focusing, Deuel, T. F. et al: *J. Biol. Chem.* 256:8896-8899, 1981, has also been successfully used to purify PDGF. Thus, a large number of options are available for the purification of the PDGF-like activity, and as discussed, sufficient quantities of tumor can be generated to follow the purification through to the end. If PDGF-like activity is not found by extraction at neutral pH, one can start with an acidic extract of the xenograft which contains acid and heat stable mitogenic activity (see Table 2). The same steps described above can be done for this material as well.

TGF-α and β can be isolated from the material which does not stick to the CM-Sephadex column. Both α and β are anionic at neutral pH; hence they do not have an affinity for the carboxy-methyl groups. The eluate from the CM-column can be concentrated, dialyzed against about 1.0 M acetic acid, and lyophilized. The residue can then be extracted with an acidic ethanol mixture (this is the first step in the published procedures for the purification of these factors, *In Cancer Cells*, Vol. 3, pp. 59-64, 1985 and *J. Biol. Chem.* 258:7155-7160, 1983) and the resulting solubilized proteins precipitated by the addition of ethanol and ether. The precipitated proteins can be resolubilized in about 1.0 M acetic acid and subject to gel filtration on a P-60 column. TGF-α activity can then be assayed by competition with [$^{125}$I]-EGF for binding to the EGF receptor of NRK and A431 cells (Table 7 and see *In Cancer Cells*, Vol. 3, pp. 59-64, 1985). TGF-β activity can be routinely assayed by synergistically enhancing EGF induced mitogenesis of sparse NRK cells (FIG. 10 and see Massague, J.: *J. Biol. Chem.* 259:9756-9761, 1984; *J. Bio. Chem.* 260:9613-9617, 1985) and confirmed by the soft agar assay with EGF. TGF-β is believed to exhibit aberrant behavior on such column and elutes at a molecular weight of approximately 13,000; TGF-α about 25-30,000. Both TGF α and β can be further purified by reverse-phase HPLC as described in *J. Biol. Chem.* 260:2636-3645, 1985, or, for TGF-β, by chromatography in the presence of urea, *J. Biol. Chem.* 258:7155-7160, 1983. Recently, a form of TGF-α has been found in a human rhabdomyosarcoma cell line, Dart, L. L. et al: *Biochemistry* 24:5925-5931, 1985, and has been partially purified by reverse-phase HPLC techniques. HPLC columns available include both a C3 and C18 column, and initial attempts at purification can use about 0.1% trifluoracetic acid buffer to load the samples, and elution can be obtained with either a propanol or acetonitrile gradient. If necessary, TGF-α can also be purified utilizing a fixed A431 cell column, followed by acid elution of the bound growth factor to the EGF receptor on the fixed cells, DeLarco, J. E. et al: *Biochemistry* 24:5925-5931, 1985. Each gram of tumor is believed to contain about 1 to about 2.5 μg of TGF-β, which is of sufficient quantity to allow for purification. It is presently believed that homogeneity of all the growth factors can be determined by gel electrophoresis and amino acid compositions.

Once purified, the growth factors can be initially characterized by determining the native and subunit molecular weights (utilizing gel electrophoresis under both native and denaturing conditions), their amino acid composition, and analysis of the main terminal group. These data can be compared to the factors already purified from platelets as well as from various transformed cell lines. This can allow for essential similarities, or differences, between TGF's from differing sources to be determined, as well as to determine if the megakaryocytic factors are different from the platelet products. Silver stained peptide mapping can also be done if sufficient quantities of pure platelet factors can be obtained for comparison purposes. In addition to determining the physical characteristics of these peptides, the biological effects of the factors on the appropriate target cells can also be determined. Assays to measure both growth stimulation or inhibition, *Proc. Natl. Acad. Sci. USA* 82:119-123, 1985 and Shipley, G. D. et al: *Proc. Natl. Acad. Sci. USA* 82:4147-4151, 1985, of both normal and transformed cells; ability to down-regulate the EGF receptor, *J. Biol. Chem.* 260:9613-9617, 1985, *J. Cell. Biol.* 100:1508-1514, 1985, Wrann, M. et al: *Science* 210:1363-1365, 1980, and Heldin, C. H. et al: *J. Biol. Chem.* 257:4216-4221, 1982; competition with EGF for binding to the EGF receptor, *In Cancer Cells*, Vol. 3, pp. 59-64, 1985; and the ability to stimulate cell growth in soft agar, can be verified to determine how these megakaryocytic factors compare to the factors previously isolated from other sources. In this manner, it is believed to be possible to completely characterize these megakaryocytic growth-like factors in terms of biological response and structure.

Figure 13:
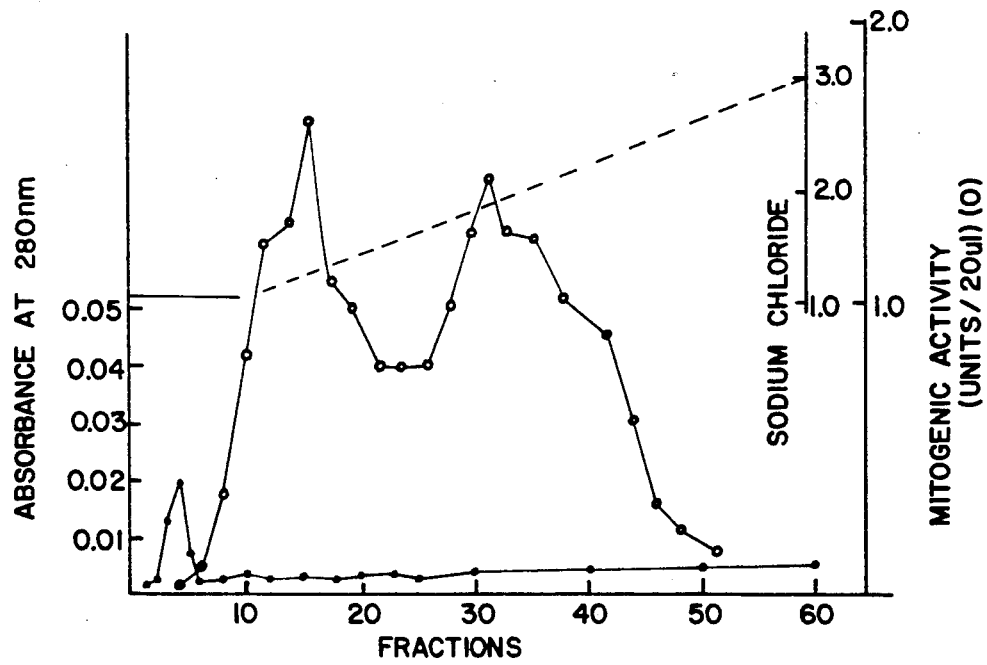
FIG. 13. Activity profile of FGF-like fractions generated by cells of this invention obtained from the nodular tissue removed from an athymic nude mouse. The activity profile was obtained from Heparin-Sepharose affinity chromatography. 300 mls of the 0.6 M NaCl eluate from the CM-Sephadex column were applied to a 10 ml column of Heparin Sepharose at 30 mls/hour. The material which did not stick to the column contained no detectable mitogenic activity. After washing with 10 mM Tris, 0.6 M NaCl, pH 7.0 to remove all non-bound proteins the column was washed with 10 mM Tris, 1.1 M NaCl, pH 7.0. At tube 10 a linear 200 ml gradient from 1.1-3.0 M NaCl, in 10 mM Tris, pH 7.0, was applied to the column. Absorbance readings at 280 nm were not detectable over most of the column eluate. Four ml fractions were collected, and 2 μl of each fraction were directly assayed for the stimulation of DNA synthesis in quiescent, 3T3 as discussed herein. Symbols: ●, A$_{280}$; O, mitogenic activity.

It is believed that both acidic and basic forms of FGF are present in this line. To demonstrate this, about 80 grams of tumor can be purified in FGF purification, Gospodarowicz, D. et al: *Proc. Natl. Acad. Sci. USA* 81:6963-6967, 1984, R. J. Ford and A. L. Maizel eds., Raven Press, N.Y., pp. 21-29, 1985, which consists of homogenizing the tumor in about 0.15 M $(NH_4)_2SO_4$, then reducing the pH to about 4.5 for about one hour, raising the pH of about 6.75, and collecting the supernatant. This supernatant can then be subjected to an ammonium sulfate fractionation, with the final pellet containing the growth factor activity. This pellet can be resuspended in about 100 mM sodium phosphate, pH about 6.0 and loaded onto a CM-Sephadex column. After an initial elution at about 0.15 M NaCl, growth factor activity is believed to be eluted at about 0.6 M NaCl. This material can then be directly applied to a Heparin Sepharose column (Pharmacia) equilibriated in about 10 mM Tris, about 0.6 M NaCl, pH of about 7.0, and growth factor activity can then be eluted with a step to 1.1 M (acidic FGF) and a gradient from about 1.1-3.0 M NaCl (basic FGF). The results of such a procedure are shown in Table 9, and FIG. 13 shows the heparin-sepharose profile. Peak I off of Heparin-Sepharose eluted at about 1.1-1.5 M NaCl and is most likely similar to acidic FGF. This material has approximately $2.4 \times 10^6$ units/mg, which corresponds to about 1 unit/400 pg material. Basic FGF has an activity of about 1 unit/50-100 pg, and it has been reported, *Methods in Enzymoloqy* 109:749-773, 1985, that acidic FGF is about 5 to 10 times less potent than basic FGF. This would indicate that the peak I from Heparin Sepharose may be greater than about 75% pure if it is acidic FGF. It is possible to further analyze this material by $C_4$ reversed phase HPLC, which is used in the final purification step of acidic FGF.

Peak II from the Heparin-Sepharose column elutes at approximately 2.0 M NaCl and may be similar to basic FGF. This material is believed to have a specific activity of about $3.4 \times 10^6$ U/mg, which corresponds to about 1 unit/300 pg. Basic FGF is active at about 50 pg/unit, so the material is at least about 16% pure, and may be higher. This material can also be analyzed by $C_4$ reverse phase HPLC.

It is also believed to be possible to purify FGF-like factor in three steps, primarily because of its high affinity for heparin-sepharose, *Proc. Natl. Acad. Sci. USA* 81:6963-6967, 1984. These steps involve homogenization of the extract in the presence of about 0.15 M ammonium sulfate and retention of the clarified extract. This material can then be dialyzed against a pH of about 6.0 buffer and loaded onto CM-Sephadex. The FGF-like factor can then be eluted at about 0.6 M NaCl, and the active fractions can then be bound to heparin-sepharose. About 1.5 M NaCl is required to elute the FGF-like factor from this column. Purity of the FGF-like factor preparations can be routinely monitored utilizing gel electrophoresis under native (2 pH's) and denaturing conditions.

In order to determine if the major growth factor present in the neutral pH extract is FGF or PDGF, the effect of the tumor extract on $BC_3H1$ muscle cell differentiation can be examined. Both acidic and basic FGF have been reported, Lathrop, B. et al: *J. Cell Biol.* 100:1540-1547, 1985, to repress creatine phosphokinase (CPK) synthesis and activity in differentiating $BC_3H1$ cells. Thus, the megakaryocyte factors can be added to confluent $BC_3H1$ cells to determine if CPK activity is reduced in extract treated cells. PDGF does not have this property, *J. Cell Biol.* 100:1540-1547, 1985; thus, if positive results are obtained, this indicates that an FGF-like factor is present in the tumor. To confirm this result, extract can also be used to support the growth of adult bovine aortic endothelium cells, as reported by Gospodarowicz, C. et al: *J. Biol. Chem.* 253:3736-3743, 1978.

TABLE 9

PURIFICATION OF AN FGF-LIKE MOLECULE FROM THE TUMOR LINE

| Fraction | Units | Protein (mg) | Specific Activity (u/mg) |
|---|---|---|---|
| After ammonium | $4 \times 10^6$ | 484 | $8.3 \times 10^3$ |
| 0.6M eluate CM-Sephadex | $3 \times 10^5$ | 24 | $1.25 \times 10^4$ |
| Peak I, Heparin-Sepharose | $1.2 \times 10^5$ | 0.05 | $2.4 \times 10^6$ |
| Peak II, Heparin-Sepharose | $1.7 \times 10^5$ | 0.05 | $3.4 \times 10^6$ |

Mitogenic units were determined as described herein. The protein concentrations for the Heparin-Sepharose fractions are based on the absorbance at 220 nm, and are thus subject to experimental error.

C) Generation Of An Antisera Against The Growth-Like Factors

An antisera against the growth-like factors is believed to be desirable for the biosynthetic studies described below. A number of laboratories have generated antisera to PDGF, *Methods in Enzymology* 109:749-773, 1985. It is believed to be possible to generate sufficient quantities of each growth factor to inject rabbits following the already published procedures of generating antibodies to PDGF, *Methods in Enzymology* 109:749-773, 1985. These workers obtained good antisera utilizing only microgram (20-200) quantities of antigen, although the PDGF was generally linked to a carrier (either Sepharose beads or keyhole limpet hemocyanin), Dockray, G. J.: *Regul. Pept.* 1:169-186, 1980, before injection. It is also believed to be possible to generate antisera to the TGF's $\alpha$ and $\beta$ in the same manner. Antisera to TGF-$\alpha$ is commercially available and may cross-react with the platelet precursor. Antibodies to TGF-$\alpha$ have not yet been fully described, and are not generally available. If injections using purified megakaryocytic TGF $\alpha$ or $\beta$ (either linked to a carrier or not) fail to generate antisera, then synthetic peptides can be utilized to generate an antisera which recognizes the TGF's. Both TGF $\alpha$ and $\beta$ have been cloned, Derynck, R. et al: In *Cancer Cells*, Vol. 3, J. Feramiso, B. Ozanne and C. Stiles, eds., Cold Spring Harbor Laboratory, pp. 79-86, 1985 and Derynck, R. et al: *Nature* 316:701-705, 1985, such that a predicted amino acid sequence can be determined. This sequence can be examined for hydrophilic sequences (which are likely to be exposed sequences) and a 15-20 residue peptide can be synthesized utilizing an automated peptide synthesizer. This peptide can then be linked to activated keyhole limpet hemocyanin, *Regul. Pept.* 1:169-186, 1980, and injected into rabbits. This procedure has been successful for the production of antibodies to many synthetic antigens. Since these antibodies can be directed against sites in the final product of the pathway they should also be able to recognize precursor molecules as well. In all cases, it is believed that antibody production can be assayed utilizing an ELISA. Samples of growth factor can be bound to a plastic micro-titer dish and putative antibody containing serum incubated with it. After washing, a horseradish peroxidase (HRP) linked goat anti-rabbit antibody can be added, and after washing again, HRP can be assayed. Sera containing positive antibodies can then be utilized for the biosynthetic studies described below. It is presently thought that the antibodies obtained can be used to immunoprecipitate their antigens, although a procedure which involves non-precipitating antibodies can also be used for such studies. Ability to immunoprecipitate can be tested by incubating antibody with iodinated growth factors (iodinations can be performed as described for the purified platelet factors, *J. Biol. Chem.* 257:5161-5171, 1982 and *J. Biol. Chem.* 260:2636-3645, 1985), and then precipitating the antibody complexes with immobilized protein A. The resulting pellet can be dissociated in an SDS buffer, boiled and then run out on a gel. Labeled bands can be located by autoradiography and compared (molecular weight) to the native proteins. Scintillation counting of the immunoprecipitate, as compared to the control, can also be determined if the antibody can precipitate the growth factor.

D) Use of Antibodies to Study the Processing and Control of the Synthesis of These Growth-Like Factors The biosynthetic pathways of PDGF, TGF-$\alpha$, and TGF-$\beta$ are heretofore not known. The processing of $P^{28sis}$, the transforming gene product of simian sarcoma virus, has been established, Robbins, K. C. et al: *Nature* 305:605-608, 1983, but its relationship to the processing of PDGF has not yet been clarified. The megakaryocytic cell line described herein presents a unique system for the study of the biosynthesis of these factors. The use of specific antiserum can enable even small quantities of growth factors to be examined, and by varying the pre-incubation time with labeled [$^{35}$S]-methionince, it should be possible to get sufficient label into the precursors. For example, 1 gram of tumor contains approximately 1 μg of TGF-β. Thus, if cells from a 200 mg piece of tumor are utilized for these studies, there is believed to be potential for labeling up to 200 ng of the growth factor, which is thought to be at a high enough level to be precipitated by the antibody and seen on a gel. About 200 ng of TGF-β corresponds to about 8 pmoles of protein. The published amino acid sequence for TGF-β contains 2 methionines per mole of protein, or 16 pmoles of methionine in 8 pmoles of TGF-β. Labeled methionine can be obtained with a specific activity as high as 1000 $C_i$/mmole. Thus, if all 16 pmoles of TGF-β are labeled, then 16 $\mu C_i$ of labeled methionine can be in TGF-β. Obviously, since the tumor is also synthesizing other proteins, not all of the incorporated methionine would be in TGF-β, but even if only about 0.1% were, then there would be greater than $2 \times 10^4$ cpm in TGF-β, which would be easily visible via fluorography.

A method of passaging the xenograft in accordance with the present invention will now be further illustrated with reference to the following example.

EXAMPLE

1. Extraction of the Orbital Tissue

The infant patient was taken to the operating room at Children's Hospital Medical Center, Cincinnati, Ohio on Sept. 27, 1984, sterilely prepped and drapped in the usual fashion. A left lower lid crease incision was marked off although a little lower than usual in order to center the incision over the tumor. The left lower lid was then infiltrated with about 2 mls of 1% Lidocaine 1:100,000 Epinephrine. After waiting for about 5 minutes, a skin incision was made, and sharp dissection was carried through the skin. Due to the excessive bleeding that was encountered, bovie cautery was utilized to go through the orbicularis to the orbital septum. Beneath the orbital septum, there was a bluish mass protruding. The orbital septum was then opened for the full width. A round domed mass with vertical striations that was bluish-red in color extending into the orbit was observed. A substantial quantity of this soft tissue was then excised using first scissors and then Takahasi cup forceps.

After the tumor biopsy had been completed, the left orbit was much softer. While there was no bleeding from the wound edges, the tumor itself continued to bleed not quickly, but in a rather sustained fashion. Electrocautery, thrombin and gelfoam were utilized, but the bleeding persisted. Since the bleeding was somewhat extensive, it was believed to be inappropriate to close the wound. The wound was therefore packed open with iodiform gauze dressing. This slowed the bleeding substantially. Several sterile eye patches were then applied, and the infant patient was awakened and taken from the operating room in satisfactory condition.

The soft tissue mass that was removed from the left orbit was taken fresh and sterilely from surgery to pathology for implantation in an athymic nude mouse.

2. Implantation of the

With respect to the implantation of the soft tissue extracted from the left orbit of the infant patient, an athymic nude mouse derived from NIH stock of Swiss background was first anesthetized lightly with an effective dose of methoxyfluorane under sterile conditions in a laminar flow hood. An adequate portion of an orbital tissue sample obtained from the surigically removed orbital mass was intimately mixed with sterile minimum essential medium (MEM). Thereafter, the tissue sample was delicately minced into about 1 mm sections. A thirteen (13) gauge trocar needle assembly was introduced subcutaneously under the skin of one of the flanks of the anesthetized nude mouse. After insertion, the stylus was removed from the trocar syringe assembly. Approximately 0.5 ml of the intimately mixed mixture containing the minced tissue sections was injected subcutaneously into the flank via the inserted trocus. Following the injection of the intimately mixed mixture into the flank, the stylus was reinserted into the trocus to introduce any mixture remaining in the trocus into the flank of the nude mouse. Approximately 0.5 mls of the intimately mixed mixture containing the minced tissue sections was also injected subcutaneously under the skin into the other flank of the anesthetized nude mouse repeating the above described procedure.

Approximately ten weeks following the implantation, the nude mouse was carefully sacrificed, and the tumor tissue that was cultivated in each flank was surgically harvested utilizing standard surgical laboratory techniques. The cells grew as a solid nodule in the subcutaneous tissue of each flank, measuring approximately 3.0 cm in greatest dimension. An adequate portion of the surgically removed tumor tissue was successfully passaged in other athymic nude mice derived from NIH stock of Swiss background by repeating the above described procedure. Once the xenograft was adapted to the athymic nude mice, the interval between passages for the tumor xenograft of this invention has been found to be approximately four weeks. All athymic nude mice were maintained in filter topped cages.

The present invention may, of course, be carried out in other specific ways than those herein set forth without departing from the spirit and essential characteristics of the invention. For instance, the continuous cell line of the present invention is described as being cultivated in athymic nude mice. Nonetheless, it should be appreciated by those versed in the art that the continuous xenograft may be cultivated in other suitable athymic nude animals, such as athymic nude guinea pigs and athymic nude rabbits. Likewise, it should be appreciated that cell culture medium is believed to be suitable for continuously cultivating the xenograft. For example, cells of the xenograft can be placed into cell culture medium following standard procedures, i.e., tissues extracted from the athymic nude mice and minced and single cells can be allowed to grow out of the explants, or tissue can be digested with collagenase/elastase to release single cells, which can then be cultured. Cells can be plated in various enriched media as previously described in, *J. Cell. Biol.* 100:565-573, 1985 and Solberg, L. A. Jr. et al: *J Cell. Phys.* 125:67-74, 1985. The media may consist of, for instance, Iscove's modification of Dulbecco's MEM, or RPMI-1640, enriched with human plasma at determined optimal concentrations as well as conditioned media from mononuclear blood cells at a concentration of about 5%. Semisolid cultures in about 0.9% methylcellulose can also be utilized to promote adaptation to tissue culture conditions. Also, it may be desirable to alternate cell growth between cell culture medium and mice for the generation of hormone producing cells. The present embodiments are, therefore, to be considered in all respects as illustrative and not restrictive and any changes coming within the meaning and equivalency range of the appended claims are to be embraced therein.

What is claimed is:
1. A xenograft deposited with the American Type Culture Collection under accession number ATCC CRL 9139.

* * * * *